(12) United States Patent
Satish et al.

(10) Patent No.: US 12,193,889 B2
(45) Date of Patent: Jan. 14, 2025

(54) SYSTEMS AND METHODS FOR TRACKING SURGICAL ITEMS

(71) Applicant: Stryker Corporation, Portage, MI (US)

(72) Inventors: Siddarth Satish, Portal Valley, CA (US); Mayank Kumar, San Jose, CA (US); Kevin J. Miller, Mountain View, CA (US); Sheetal D. Jantikar, Fremont, CA (US); Daniel Goodman, Mountain View, CA (US); Andrew T. Hosford, Idaho Falls, ID (US); Charles Peterson Carroll, Berkeley, CA (US)

(73) Assignee: Stryker Corporation, Portage, MI (US)

( * ) Notice: Subject to any disclaimer, the term of this patent is extended or adjusted under 35 U.S.C. 154(b) by 356 days.

(21) Appl. No.: 17/616,054

(22) PCT Filed: May 29, 2020

(86) PCT No.: PCT/US2020/035189
§ 371 (c)(1),
(2) Date: Dec. 2, 2021

(87) PCT Pub. No.: WO2020/247258
PCT Pub. Date: Dec. 10, 2020

(65) Prior Publication Data
US 2022/0296332 A1    Sep. 22, 2022

Related U.S. Application Data

(60) Provisional application No. 62/856,701, filed on Jun. 3, 2019.

(51) Int. Cl.
*A61B 90/00* (2016.01)
*A61B 5/00* (2006.01)
(Continued)

(52) U.S. Cl.
CPC ............ *A61B 90/361* (2016.02); *A61B 5/742* (2013.01); *G06F 18/2413* (2023.01);
(Continued)

(58) Field of Classification Search
CPC .................. A61B 90/361; A61B 5/742; A61B 2090/0805; A61B 90/90;
(Continued)

(56) References Cited

U.S. PATENT DOCUMENTS 7,180,014 B2    2/2007  Farber et al.
8,897,523 B2    11/2014 Satish et al.
(Continued)

FOREIGN PATENT DOCUMENTS

CN    202505475 U    10/2012
CN    103988057 A    8/2014
(Continued)

OTHER PUBLICATIONS

International Search Report for Application No. PCT/US2020/035189 dated Aug. 14, 2020, 1 page.
(Continued)

*Primary Examiner* — Brandon J Miller
(74) *Attorney, Agent, or Firm* — Howard & Howard Attorneys PLLC

(57) ABSTRACT

Described herein are methods and systems for tracking surgical items. The methods may be performed by one or more processors, and may include receiving a first count of surgical items, receiving one or more images, wherein each image is a field of view comprising one or more surgical items, determining a second count of surgical items based at least in part on the one or more received images, and providing a notification based on the comparison between the first count of surgical items and the second count of surgical items.

20 Claims, 15 Drawing Sheets

(51) Int. Cl.
*G06F 18/2413* (2023.01)
*G06V 10/764* (2022.01)
*G06V 10/82* (2022.01)
*G06V 20/20* (2022.01)

(52) U.S. Cl.
CPC ............ *G06V 10/764* (2022.01); *G06V 10/82* (2022.01); *G06V 20/20* (2022.01); *A61B 2090/0805* (2016.02)

(58) Field of Classification Search
CPC ........ A61B 2090/0804; G06F 18/2413; G06V 10/764; G06V 20/20; G06Q 10/0875; G16H 15/00; G16H 20/40; G16H 40/63; G16H 40/67
See application file for complete search history.

(56) References Cited

U.S. PATENT DOCUMENTS

| | | | |
|---|---|---|---|
| 9,962,169 B2 | 5/2018 | Garcia et al. | |
| 2002/0049650 A1 | 4/2002 | Reff | |
| 2004/0031626 A1 | 2/2004 | Morris et al. | |
| 2004/0186683 A1* | 9/2004 | Farber .................. | G06Q 10/087 606/1 |
| 2007/0083170 A1 | 4/2007 | Stewart et al. | |
| 2007/0125392 A1 | 6/2007 | Olson et al. | |
| 2009/0317002 A1 | 12/2009 | Dein | |
| 2012/0000804 A1 | 1/2012 | Barnes et al. | |
| 2016/0220316 A1 | 8/2016 | Daon et al. | |
| 2017/0143284 A1* | 5/2017 | Sehnert ................ | A61B 6/5258 |
| 2017/0186160 A1 | 6/2017 | Satish et al. | |
| 2019/0388182 A1 | 12/2019 | Kumar et al. | |

FOREIGN PATENT DOCUMENTS

| | | | | |
|---|---|---|---|---|
| JP | 2002282200 A | | 10/2002 | |
| JP | 2018068863 A | | 5/2018 | |
| WO | 2013009709 A2 | | 1/2013 | |
| WO | 2018132527 A1 | | 7/2018 | |
| WO | WO-2018125812 A1 | * | 7/2018 | ............ A61B 90/92 |
| WO | 2019040770 A1 | | 2/2019 | |

OTHER PUBLICATIONS

Kranzfelder et al., "Real-Time Monitoring for Detection of Retained Surgical Sponges and Team Motion In Surgical Operation Room Using Radio-Frequency Identification (RFID) Technology: A Preclinical Evaluation", Journal of Research, vol. 175, Issue 2, Jun. 15, 2012, 8 pages.
English language abstract and machine-assisted English translation for JP 2002-282200 A extracted from espacenet.com database on Jul. 2, 2024, 9 pages.
English language abstract and machine-assisted English translation for JP 2018-068863 A extracted from espacenet.com database on Jul. 2, 2024, 18 pages.
English language abstract for CN 103988057 A extracted from espacenet.com database on Jul. 31, 2024, 1 page.
English language abstract for CN 202505475 U extracted from espacenet.com database on Jul. 31, 2024, 2 pages.

* cited by examiner

Triton Count Compliance Report
05/13/2019 to 05/19/2019

| Case Index Number | Case Location | Case Start Time | Case End Time | Case Duration | Sponges Counted | Final Count Performed by |
|---|---|---|---|---|---|---|
| 1 | OR 1 | 5/13/2019 07:53:19 PST | 5/13/2019 09:59:32 PST | 126 minutes | 30 | Jane Doe |
| 2 | OR 1 | 5/13/2019 07:53:19 PST | 5/13/2019 09:59:32 PST | 126 minutes | 30 | Jane Doe |
| 3 | OR 1 | 5/13/2019 07:53:19 PST | 5/13/2019 09:59:32 PST | 126 minutes | 30 | Jane Doe |
| 4 | OR 1 | 5/13/2019 07:53:19 PST | 5/13/2019 09:59:32 PST | 126 minutes | 30 | Jane Doe |

FIG. 16

SYSTEMS AND METHODS FOR TRACKING SURGICAL ITEMS

PRIORITY CLAIM

This application claims the priority benefit of U.S. Provisional Patent Application No. 62/856,701, filed Jun. 3, 2019 and titled "SYSTEMS AND METHODS FOR TRACKING SURGICAL ITEMS," which is incorporated herein by reference in its entirety.

TECHNICAL FIELD

The subject matter disclosed herein generally relates to the technical field of medical care, and more specifically to new and useful systems and methods for tracking surgical items. Such systems include special-purpose machines that facilitate tracking of surgical items, including software-configured computerized variants of such special-purpose machines and improvements to such variants, and to the technologies by which such special-purpose machines become improved compared to other special-purpose machines that facilitate tracking of surgical items.

BACKGROUND

Tracking surgical items during medical procedures may be important for reducing the risk of items being inadvertently retained in a patient. Current methods of ensuring that surgical items are not retained in a patient revolve around manual tracking and counting of surgical items. However, manual counts are often incorrect due to fatigue of medical staff, complex operations that make keeping track of surgical items difficult, poor counting systems, and items sticking together or being otherwise obscured. Further, compliance with established protocols may be imperfect, particularly during long or complicated procedures. Thus, retained surgical items remain a significant problem during medical procedures. Items left in a patient during surgery pose significant health risks to patients and add to the overall time and cost of medical care. Thus, new and improved methods and systems for tracking surgical items during medical procedures may be desirable.

BRIEF DESCRIPTION OF THE DRAWINGS

FIG. 16 is a diagram depicting a summary report, according to some example embodiments.

DETAILED DESCRIPTION

Figure 1:
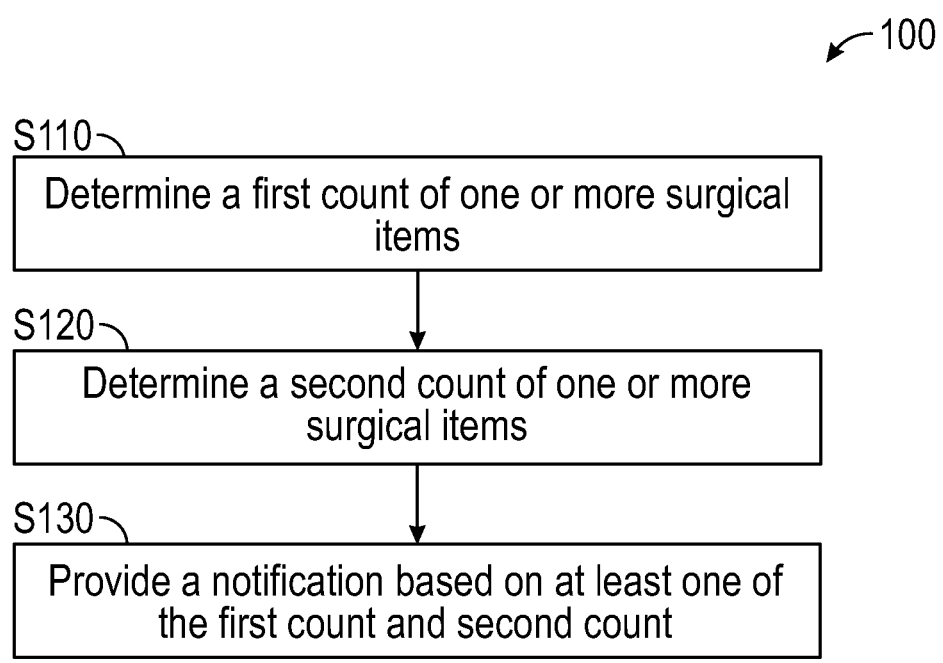
FIG. 1 is a schematic block diagram depicting a method of tracking surgical items, according to some example embodiments.

Example methods (e.g., algorithms) facilitate tracking surgical items, and example systems (e.g., special-purpose machines configured by special-purpose software) are configured to facilitate tracking surgical items. Examples merely typify possible variations. Unless explicitly stated otherwise, structures (e.g., structural components, such as modules) are optional and may be combined or subdivided, and operations (e.g., in a procedure, algorithm, or other function) may vary in sequence or be combined or subdivided. In the following description, for purposes of explanation, numerous specific details are set forth to provide a thorough understanding of various example embodiments. It will be evident to one skilled in the art, however, that the present subject matter may be practiced without these specific details.

Any one or more of the example methods and systems discussed herein may be used to track (e.g., identify, account for, monitor, etc.) one or more surgical items. For example, such methods and systems may be used to compare counts of surgical items at various time points to determine whether all surgical items are accounted for. Such methods and systems may utilize computational techniques such as computer vision, machine learning, deep learning, or any suitable combination thereof, to provide accurate identification and counting of surgical items. Employing sophisticated computational techniques may, for example, improve the accuracy of surgical item counting, improve compliance with counting protocols, streamline the process of accounting for surgical items, reduce overall cost and time associated with the risk of retained surgical items, or any suitable combination thereof. Accurate accounts of surgical items introduced into a medical procedure may help avoid inadvertent retention of surgical items in a patient following a medical procedure. Tracking surgical items may also provide helpful information regarding the use of surgical items during procedures, compliance with established protocols, or both, and may aid users in triggering various responses where particular indications are present.

The methods and systems described herein may be used in a variety of settings, including in a hospital or clinic setting (e.g., an operating or clinical setting), a military setting (e.g., a battlefield), or other suitable medical treatment setting. Although the methods and systems described herein are primarily described with reference to tracking surgical items, such as surgical textiles (e.g., surgical sponges or a pads of surgical gauze), it should be understood that in other variations, such methods and systems may additionally or alternatively be used to track other items (e.g., surgical instruments or equipment).

Although example methods are primarily described herein in terms of tracking surgical textiles, such methods may be applied to any item used in a medical procedure. For example, such methods may comprise identifying, accounting for, or otherwise tracking other surgical items such as scalpels, scissors, sutures, needles, gauze, bandages, or any other suitable item. Accounting for various types of surgical items may also involve the use of multi-compartment containers used to count surgical items such as surgical textiles, Such multi-compartment containers may be termed "counting bags." However, in some example embodiments, methods of tracking surgical items may not utilize counting bags. Computational techniques may be applied to count items without the use of counting bags and may be used to count items grouped or organized in any suitable manner.

Overview of Examples

Described herein, inter alia, are example methods for tracking surgical items. The methods may be performed by one or more processors. In some example embodiments, a method for tracking surgical items includes receiving a first count of surgical items, receiving one or more images, where each image depicts of a field of view comprising one or more surgical items, and determining a second count of surgical items based at least in part on the one or more received images. Some example embodiments of the methods discussed herein may also include providing a notification based on the first count of surgical items, the second count of surgical items, or both. For example, the notification may be provided based on a comparison between the first count of surgical items and the second count of surgical items. In some example embodiments, the first count may generally be determined before a medical procedure, and the second count may generally be determined during or after a medical procedure.

The receiving of the first count of surgical items may comprise identifying one or more surgical items depicted in an image. For example, the identifying of one or more surgical items may include the use of computer vision, machine learning, other computational techniques, or any suitable combination thereof. In some example embodiments, the receiving of the first count of surgical items may be based at least in part on detecting a weight of one or more surgical items. In certain example embodiments, the first count of surgical items may be determined based at least in part on a user input. The determining of the second count of surgical items may include identifying one or more surgical items depicted in one or more received images. One or more of the received images may, for example, be a depth image (e.g., an infrared depth image), a color image, or other suitable kind of image. In some example embodiments, the identifying of one or more surgical items depicted in the one or more received images includes identifying and characterizing a container that comprises at least one compartment and is depicted in the one or more images. The characterizing of the container may include determining one or more parameters of the container. The determining of the one or more parameters of the container may, for example, include quantifying the one or more compartments in the container, determining the geometrical arrangement of the one or more compartments in the container, determining the presence or absence of a surgical item in at least some (e.g., each) of the one or more compartments, or any suitable combination thereof. In various example embodiments, the determining of the second count of surgical items may additionally or alternatively be based at least in part on detecting a change in weight of a container configured to hold one or more surgical items.

The determining of the second count of surgical items may include updating a current index value of surgical items. Some example embodiments of the method discussed herein include displaying the current index value of surgical items on a display (e.g., on a graphical user interface of a mobile computing device). Certain example embodiments of such methods comprise prompting a user to verify the accuracy of the first count of surgical items, the second count of surgical items, or both counts of surgical items. Various example embodiments of these methods include displaying the first count of surgical items, the second count of surgical items, the notification, or any suitable combination thereof, on a display (e.g., a display screen). For example, some example embodiments of the methods discussed herein include providing a summary report of tracked surgical items. In certain example embodiments, the method includes providing a notification based on the comparison between the first count and the second count, and may include generating an alert in response to the first count not matching the second count. The alert may be in accordance with a predetermined protocol. For example, the alert may display the predetermined protocol, guide the user through the protocol, or both.

Also described herein, inter alia, are example systems for use in identifying, tracking, and accounting for surgical items. Systems for tracking surgical items may include one or more processors. For example, one or more processors may be configured to receive a first count of surgical items, receive one or more images, where each image depicts of a field of view comprising one or more surgical items, and determine a second count of surgical items based at least in part on the one or more received images. The one or more processors may also provide a notification based on the first count of surgical items, the second count of surgical items, or both. For example, the notification may be provided based on a comparison of the first count of surgical items to the second count of surgical items. The one or more processors may also be configured to identify one or more surgical items depicted in one or more of the received images. One or more of the surgical items may be a surgical textile (e.g., a surgical sponge or a piece of surgical gauze). At least one of the received images may be a depth image. In some example embodiments, the depth image is an infrared image. At least one of the received images may be a color image. The one or more processors may also be configured to identify and characterize a container that comprises at least one compartment and is depicted in the one or more images. In some example embodiments, the one or more processors are be configured to determine one or more parameters of the container. Example parameters include a geometrical arrangement of the one or more compartments in the container, the presence or absence of a surgical item in each of the one or more compartments, or both. The container may be a flexible container comprising a backing and a plurality of pockets arranged in a grid (e.g., a rectangular grid). The pockets of the container may be transparent. The backing of the container may be comprised of opaque material, colored material, or any suitable combination thereof.

Certain example embodiments of the systems discussed herein further include an optical sensor configured to generate the images received by the one or more processors. In some example embodiments, systems include a display screen configured to display a summary report of tracked surgical items. The display screen may also be configured to display the notification, for example, based on the comparison between the first count and the second count. According to some example embodiments, the notification includes an alert in accordance with a predetermined protocol if the first count does not match the second count. According to certain example embodiments, at least one of the one or more processors is included in a mobile computing device. The mobile computing device may be removably mounted to a stand or other suitable mounting device.

Certain example embodiments of the methods discussed herein include determining the presence of one or more surgical items, and such methods may be performed by one or more processors. For example, the tracking of surgical items may include receiving an image of a field of view, wherein the field of view includes one or more surgical items, determining the presence of the one or more surgical items in the image, and providing an indication of the determined presence of the one or more surgical items in the image. Certain example methods further include quantifying the one or more surgical items in the image based on at least one machine learning model. In some example embodiments, the machine learning model may incorporate one or more deep learning techniques. Other computational techniques may additionally or alternatively be used to determine the presence of one or more surgical items in the image. Example methods may include detecting an item in each of one or more compartments of a container. The determining of the presence of one or more surgical items may include detecting the presence of a container in an image, wherein the container comprises a plurality of compartments, and each compartment is configured to receive at least one respective surgical item. The one or more surgical items may include one or more surgical textiles, one or more surgical instruments, or any suitable combination thereof. According to some example embodiments, the methods discussed herein include classifying each compartment of the container based on the presence of absence of a surgical item. The providing of the indication of the determined presence of a surgical item may include providing an indication of a determined presence of at least one surgical item depicted in an image.

Example Methods for Tracking Surgical Items

Described herein are example methods for tracking (e.g., identifying, detecting, accounting for, detecting objects over time, etc.) surgical items, such as during a medical procedure. Such methods for tracking surgical items may use various computational components, such as processors, optical detection systems, computer vision, machine learning, deep learning algorithms, or any suitable combination thereof, to automate and streamline processes of identifying, tracking, and accounting for surgical items. FIG. 1 provides a schematic depiction of some example embodiments of a method 100 of tracking surgical items in a medical procedure. The method 100 may comprise determining a first count of one or more surgical items S110, determining a second count of one or more surgical items S120, and providing a notification S130 based on at least one of the first count of one or more surgical items and the second count of one or more surgical items. For example, the notification may be provided based on a comparison between the first count and the second count (e.g., to confirm reconciliation between the first count and the second count, to track progress toward incrementally increasing counts until the first count and the second count are reconciled, to alert a user when the first and second count fail to be reconciled (e.g., fail to match), or any suitable combination thereof).

Figure 2:
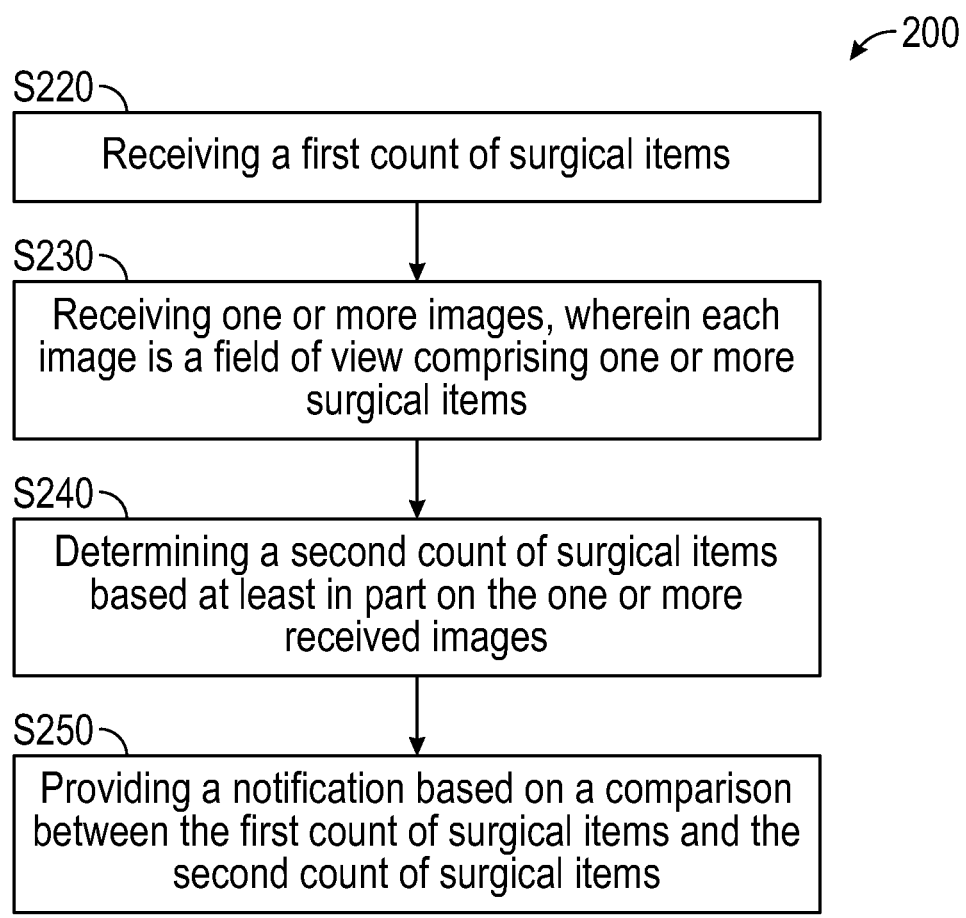
FIG. 2 is a schematic block diagram depicting a method of tracking surgical items, according to some example embodiments.

Additional example embodiments of a method 200 for tracking surgical items are shown in FIG. 2. The method 200 may include, at one or more processors, receiving a first count of surgical items S220, receiving one or more images S230, wherein each image is a field of view comprising one or more surgical items, and determining a second count of surgical items S240 based at least in part on the one or more received images. The method 200 may include providing a notification S250 based on a comparison between the first count of surgical items and the second count of surgical items.

In some example embodiments, the first count of surgical items may be associated with a first time, while the second count of surgical items may be associated with a second time that is after the first time. For example, a first count of surgical items may be an "initial count" and correspond to a number of surgical items introduced into the operating room, removed from packaging, or otherwise prepared for use during a medical procedure. A second count of surgical items may correspond to a number of surgical items that are used during a medical procedure. As described herein, the term "used" refers to items intended for discard, and a used item may be soiled or non-soiled (e.g., with blood, other fluids, other content, or any suitable combination thereof). A second count may be measured at an intermediate time point or measured at a "final" time point at the end of a procedure (e.g. after procedures are completed but prior to surgical closure) as a "final count".

Maintaining (e.g., updating) and comparing counts of surgical items at various time points in a medical procedure may facilitate accurate accounting for surgical items. This may provide the benefit of preventing instances of surgical items being retained in a patient. In some example embodiments, methods of comparing counts may comprise reconciling an initial count of surgical items with the final count of surgical items (e.g., checking whether the initial count matches the final count). This reconciliation may provide the benefit of determining whether all surgical items are accounted for prior to surgical closure. According to certain example embodiments, methods discussed herein may further comprise providing users with a notification based on whether the first count matches the second count. If the first count and the second count do not match, such methods may comprise notifying or otherwise alerting a user to take one or more predetermined actions (e.g., search for a surgical item not accounted for).

As described above, any one or more of the methods described herein for tracking (e.g., identifying and/or detecting) surgical items may be implemented using one or more computational techniques. In some example embodiments, such methods of tracking surgical items involve the use of computer vision, machine learning, deep learning algorithms, or any suitable combination thereof. For example, computer vision may include one or more computational techniques of identifying objects in an image, series of images, or frame of a video. As another example, machine learning or deep learning techniques may involve training and using computational mathematical models to perform a particular task by identifying complex patterns associated with surgical items in the image (e.g., depicted in a still image, in a series of images, or in a frame of a video). In some machine learning techniques, a computer algorithm "learns" to perform a complex task by being trained on a varied dataset comprising a large number of labeled images (e.g., labeled with features associated with surgical items). Labeled datasets may be used to train a machine learning model to recognize certain patterns, which enable the model to perform the programmed task with high level of accuracy. In some implementations, even as the model is in use, it may continue to learn by updating the algorithm based on the real-world data it receives over time and continuously updating the parameters to improve object tracking, detection performance, or both. For example, machine learning can be used to generate a model that identifies one or more items, counts one or more items, or both. Deep learning is a type of machine learning that may, for example, be based on artificial neural networks that uses multiple layers or analysis to extract relevant features from input data to detect, identify, or otherwise track surgical items. As used herein, the term "computational techniques" refers to any one or more of the methods described herein and should not be limited to describing one technique. Furthermore, in some implementations, aspects of multiple computational techniques may be combined. For example, one or more computer vision techniques may be implemented via machine learning, deep learning, or both. For example, computer vision used to identify a surgical item may utilize a machine learning algorithm, a deep learning algorithm, or both, to perform the identification of a surgical item.

According to various example embodiments, a mobile computing device, such as a mobile phone or tablet, is used to carry out one or more various aspects of the methods discussed herein for tracking surgical items. For example, a software application executable by one or more processors on a mobile device may be used to perform one or more operations that include determining a first count, determining a second count, comparing a first count to a second count, and notifying a user based on the comparison. One or more processors on a mobile device may be configured to analyze images. One ore more processors of the mobile device may be configured to perform machine learning algorithms, computer vision techniques, deep learning algorithms, or any suitable combination thereof, in connection with any one or more of the methods described herein. In some example embodiments, a mobile application is configured to perform all of the steps in a method of tracking surgical items and to display information to one or more users based one or more of the operations (e.g., steps) in the performed method. Implementing one or more of such methods of tracking surgical items on a mobile device may provide the benefits of automating and streamlining the process of accounting for surgical items, as well as providing an additional virtual presence to guide users through the appropriate accounting protocols to facilitate an accurate accounting of surgical items. Further, implementing computational techniques on a mobile device may aid in making improved methods of tracking surgical items highly accessible and intuitive to use. In other example embodiments, some or all of the operations of a method may be performed using one or more external processors. For example, a mobile device may be used to take one or more images, receive information, and display information, and an external processor may be used to perform an analysis of the one or more images using one or more machine learning algorithms.

Examples of Determining a First Count

Some example embodiments of methods for tracking surgical items include receiving a first count of surgical items. In some implementations, the first count may establish a corresponding number of one or more surgical items that have been introduced or otherwise prepared for intended use in a medical procedure (e.g., introduced into the operating room, removed from packaging, or both). The first count may be established once at any point during the procedure. In some implementations, the first count is or includes the number of surgical items introduced prior to or at the beginning of the surgical procedure. In some implementations, the first count is subsequently updated throughout the course of the procedure (e.g., as surgical items are introduced into the operating room, removed from packaging, or both). For example, one package of surgical items may be introduced into the operating room and removed from packaging at the start of a procedure (e.g., before any operational steps on a patient begin). Subsequently, at a point during the medical procedure, such as while an operation is being performed, a second package of surgical items may be retrieved, introduced into the operating room, and have its surgical items removed from packaging. Thus, the first count may be updated (e.g., incremented) with the number of surgical items in the second package. Any number of surgical items may be introduced at any point during a procedure, and the first count may be updated each time a new set of surgical items is introduced.

Establishing the first count of items may provide the benefit of facilitating an accounting of all surgical items at the end of the procedure. For example, the methods discussed herein may include comparing a count of items present at the end of a procedure to the first count to determine if all surgical items are accounted for (e.g., as opposed to being, for example, retained within a patient). Various suitable methods may be used to establish the first count of surgical items, such as those described below. In some implementations, establishing the first count of items may be performed manually. For example, the first count of surgical items may be received as a manual input or other user input. As another example, the first count of surgical items may additionally or alternatively be established by one or more processors (e.g., through one or more computational techniques, as described below). Computational techniques for establishing the first count may, for example, provide the benefit of establishing the first count with increased accuracy and reduced user error, and streamlining the process of determining the first count, compared to manual methods.

In some example embodiments, as described above, the first count of items may be received as a user input. For example, establishing the first count of surgical items may involve manual counting techniques. A user may manually count out a plurality of surgical items to determine the first count and provide the first count through a user interface. For example, a user may receive a package containing one or more surgical items, remove the items from packaging, and count out the surgical textiles as he or she separates the textiles from each other, such as while arranging them on a surface, such as a table. In some implementations, the manual count is input by a user into a computational system (e.g., manual entry on a keypad or touchscreen, recitation, etc.). For example, the user may input the manual count into a computation system via a mobile application executable on a mobile computing device. In some implementations, a mobile application may prompt a user to enter a manual count.

In some example embodiments, the determining of the first count of surgical items may additionally or alternatively involve the use of computer vision, machine learning, deep learning, other computational techniques, or any suitable combination thereof. For example, establishing the first count may include analyzing an image to identify one or more surgical items, count one or more surgical items, or both. An image of one or more surgical items to be counted in the first count may be obtained using any suitable imaging device. For example, an imaging system, such as on a mobile computing device (e.g., mobile telephone, tablet, etc.), may be used to capture an image of one or more surgical items. The image may be a still image or a frame from a video feed. In some implementations, multiple images (e.g., multiple frames from a video feed) are processed to determine the first count of surgical items. While in some implementations the image is or includes a color image, in other implementations the image is or includes a depth image (e.g., infrared, stereoscopic, ultrasound, etc.), hyperspectral image, or other suitable kind of image. Furthermore, multiple images of the one or more surgical items may be simultaneously, near-simultaneously, or sequentially obtained, and may be of different types (e.g., a color image combined with a depth image). Generally, one or more processors may be configured to receive the one or more images, analyze the one or more images, or both. Furthermore, the one or more processors may implement computational techniques (e.g., using computer vision, machine learning, deep learning, or any suitable combination thereof) to identify one or more surgical items, count one or more surgical items, or both, where one or more surgical items are depicted in an image received by the one or more processors. Such processors may be implemented in computing device such as a mobile computing device. In some implementations, a mobile application executable on a computing device may be used in conjunction with any of the variations described below to obtain, receive, and process data related to the first count of surgical items.

In some example embodiments, the determining of the first count of surgical items using image analysis includes the following operations. A user obtains a package containing one or more surgical items, such as surgical textiles, and brings the package into the operating room. The user may remove the one or more surgical items from their packaging, separate the surgical items, and arrange them on a surface, such as a table. The user may then use an imaging system, such as the camera on a mobile computing device, to obtain one or more images of the surgical items on the table. A processor of the mobile computing device then analyzes the image to identify the separate surgical items in the image, count or otherwise quantify the number of surgical items in the image, or both. For example, the first count of surgical items may be determined using computational techniques, such as computer vision, machine learning, deep learning techniques, or any suitable combination thereof, including any one or more of those described in further detail below with respect to determining a second count of surgical items. The processor may store information regarding the detection and counting of surgical items in memory. In some implementations, the determining of the first count includes updating the first count by adding the number of surgical items the processor counted in the image to a number of surgical items previously counted (e.g., surgical items depicted in an image taken at a prior time point). Additionally or alternatively, the determining of the first count may include counting the number of surgical items in an image taken at one time point (e.g., where no surgical items have been previously counted).

In some example embodiments, one or more computational techniques include detecting a characteristic arm motion of a user to determine the first count of surgical items. A characteristic arm motion may be characterized in any suitable manner. For example, detecting the characteristic arm motion may include identifying a "dealing" motion by a user as they separate surgical items, since it is often the case in surgical procedures that medical personnel will "deal out" surgical textiles onto a surface to count them as they remove surgical textiles from packaging. An imaging system with a camera may be positioned such that the system views the arm motion of a user (e.g., frontal view, side view, overhead view, or any suitable combination thereof), and a processor may receive still frame images or video from the imaging system. The sweeping (e.g., dealing out) arm motion as the user removes the surgical textile from packaging to lay the surgical textile out on a surface may be detected using the imaging system and computational analysis (e.g., performed by the processor). Thus, each arm motion detected by processor may correspond to a counted surgical item, and may contribute to the first count of surgical items.

In certain example embodiments, one or more computational techniques utilize weight information to determine the first count. For example, surgical items may be sequentially placed onto a scale, and the incremental weight change may be detected by one or more processors in order to determine the first count of surgical items. That is, based on the incremental weight change that occurs when an additional surgical item is placed onto a scale, a processor may be able to detect the presence of the additional surgical item. Each time the processor detects an incremental weight change, the processor may increase the first count.

Additionally or alternatively, according to some example embodiments, a plurality of surgical items may be placed onto a scale, and information about the weight of each individual surgical item may be used to determine the first count of surgical items. For example, a user may be prompted through a user interface to enter a type of surgical item to be weighed. The type of surgical item may be entered, for example, by searching through a database of existing surgical item types, navigating a hierarchal menu of surgical item types, or entering a surgical item type. Surgical item types may be categorized or otherwise distinguished, for example, based on function (e.g., textile, type of surgical instrument, etc.) or item-specific characteristics such as brand, size, material, etc. Additionally or alternatively, the surgical item type may be determined based on other identification (e.g., scanning a barcode or a radio-frequency identification (RFID) tag associated with the surgical item type). A processor in communication with the scale may receive information regarding the weight of a single surgical item, based on the received surgical item type. Accordingly, information about the weight of the surgical item may be manually input by a user, stored in memory in a lookup table, or obtained by scanning an electronic tag, such as a barcode or RFID tag, on the surgical item. Based on the information about the weight of the single surgical item, the processor may determine the number of surgical items on the scale by dividing the total weight of a plurality of surgical items by the known weight of the single surgical item.

Figure 3:
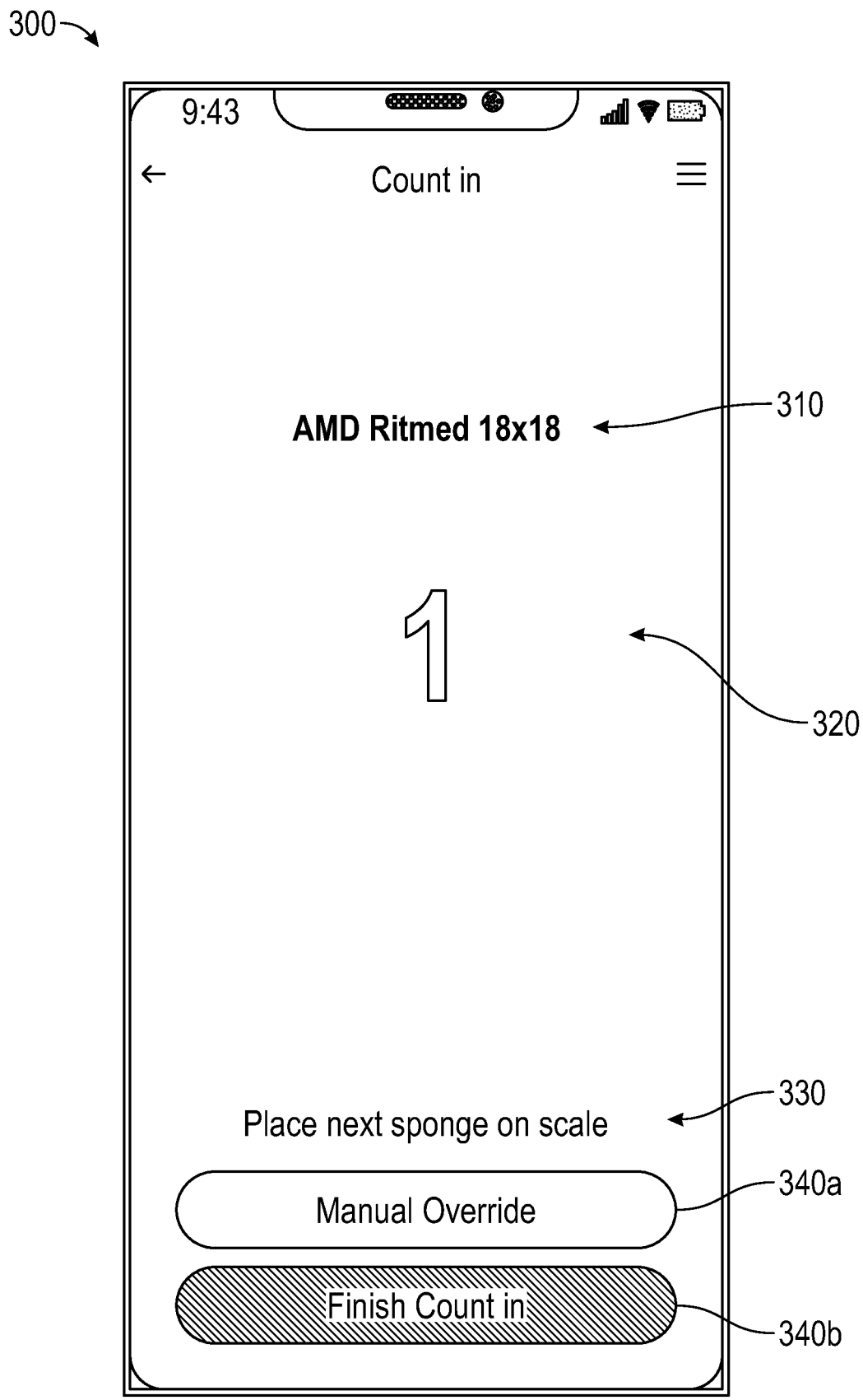
FIG. 3 is a diagram depicting a graphical user interface showing information related to a first count of surgical items, according to some example embodiments.

As described above, a mobile application may be used in conjunction with one or more weight-based methods of determining the first count. FIG. 3 depicts an example embodiment of a graphical user interface 300 depicting information related to determining the first count via use of a scale. The graphical user interface in FIG. 3 displays the type of surgical item 310 being counted, and the current determination 320 of the first count. The graphical user interface 300 instructs a user to place a new surgical item on the scale 330. Further, the graphical user interface 300 provides selectable icons 340a and 340b to allow the user to manually override (340a) the first count and provide a manual count, and to finish (340b) the first count (e.g., indicate that all surgical items of the selected type have, at least for now, been counted toward the first count).

In some example embodiments, one or more computational techniques of determining the first count additionally or alternatively involve the use of scannable tags (e.g., RFID, bar codes, or any suitable combination thereof). For example, surgical items may include individual RFID tags that may be scanned as surgical items are introduced into the operating room, as they are removed from packaging, or at some other time point before use. In other situations, a package of surgical items may include a scannable tag configured such that one scan of the scannable tag may account for multiple surgical items. For example, a package of surgical items may include one scannable tag that communicates the number of items in the package to the processor for inclusion in the first count. Thus, methods of determining the first count may include scanning a tag on a surgical item or on a package of surgical items to determine the first count.

The determining of the first count may include one or more of the methods described above. In some example embodiments, multiple methods of determining the first count are used to verify the accuracy of the first count. Methods of determining the first count may be combined in any suitable manner. For example, a weight-based method, such as detecting an incremental weight change in a scale or utilizing known weight information about a singular surgical item, may be combined with an image-based method, such as using one or more computational techniques to identify and count surgical items in an image. As another example, an image-based method may be combined with one or more computational techniques involving recognition of a characteristic motion of a user. One or more manual counting techniques may be used to verify any one or more of the methods described herein for determining the first count. In some example embodiments, a mobile application prompts a user to verify a determination of the first count generated using a computational technique. In some example embodiments, as described above with respect to FIG. 3, the method includes allowing a user to override an automatic or computational determination of the first count if the user determines that the first count is inaccurate.

In some example embodiments, the determining of the first count of surgical items includes categorizing the surgical items. The determining of the first count may include distinguishing different surgical items, determining different types of the same surgical item, or both. For example, different types of surgical textiles may be distinguished from each other (e.g., by material, function, size, brand, or any suitable combination thereof). As another example, two differing types of surgical items may be distinguished from each other (e.g., distinguishing a scalpel from a pair of scissors). Any suitable method, including any one or more of the computational techniques described herein, may be used to determine the type of one or more surgical items, such as the type of one or more surgical textiles). In some implementations, the determining of the first count includes indicating separate categories of first counts, in addition to a total first count of all counted surgical items regardless of type. For example, the first count may include a type-specific first count of 18 inch×18 inch surgical textiles, and another type-specific first count of 4 inch by 4 inch surgical textiles.

Any of the methods described herein for determining the first count may additionally or alternatively be used to determine the second count. Similarly, any of the methods described herein for determining the first count may additionally or alternatively be used to perform any other suitable analysis of surgical items (e.g., tracking used items, tracking unused items, or both, as described below).

Examples of Determining a Second Count

Some example embodiments of methods for tracking surgical items further comprise determining a second count of surgical items. As described above, the second count of surgical items may be compared to the first count of surgical items. The second count may be determined at any suitable time point in a procedure (e.g., a medical procedure, such as a surgical procedure). For example, the second count may be an "intermediate count" that is determined at an intermediate time point during a procedure, between a starting time point and an ending time point of the procedure. The determining of the intermediate count may comprise updating an index counter of surgical items during (e.g., throughout) the course of a procedure (e.g., as surgical items are used or otherwise designated as intended for discard). The intermediate count may be compared to the first count to help indicate how many remaining "used" surgical items remain in the field during the course of the procedure. The second count may also be a final count at the end of the procedure. It may be desirable to compare the final count to the first count to determine whether all surgical items have been accounted for, and to limit the risk that a surgical item was retained in a patient undergoing the procedure. The end of the procedure may be denoted in any suitable manner. For example, the end of the procedure may be at a time when the patient is ready for removal from the operating room (e.g. after the surgical site has been closed), or before a surgical site of the patient has been closed, but after operational procedures are completed.

Any of the methods described herein for determining the second count may additionally or alternatively be used to determine the first count. Similarly, any of the methods described herein for determining the second count may additionally or alternatively be used to perform any other suitable analysis of surgical items (e.g., tracking used items, tracking unused items, or both, as described below).

Examples of Using Counting Bags

In some example embodiments, counting surgical items involves the use of counting bags to account for surgical textiles. The use of counting bags may facilitate accurate and methodical counting of surgical textiles, and reduce the risk of a surgical item being retained in a patient. One or more users may place surgical textiles that are designated to be discarded into the pockets of a counting bag to facilitate efficient and accurate counting. Furthermore, discarding of surgical textiles or other items may, in some example embodiments, include a multi-step item collection process. For example, in some operating room procedures, after surgical textiles are used in a procedure, they may be accumulated in one or more collection containers (e.g., a "kick bucket" in the example form of a metal bucket lined with a plastic liner placed near an operating table or in another location within the operating room). During or after the procedure, one or more medical personnel may subsequently remove surgical textiles from the one or more collection containers, and place the surgical items into counting bags for counting. In other example embodiments, surgical textiles may be placed directly into counting bags, without the use of a separate collection container. All surgical textiles that are used in a procedure may be accounted for using the counting bags. As described above, the term "used" is not limited to surgical textiles that were used to soak up blood or other fluids, but may refer to any surgical textile that was introduced into the operating room and subsequently deemed discardable or otherwise designated to be discarded. According to some example embodiments, manual counting of surgical textiles involves placing surgical items, such as surgical textiles, into the compartments of the counting bag according to a specific protocol, such as described below. One or more methods of accounting for surgical items, such as those implementing one or more computational techniques, may be used to automate and reduce the error associated with manual counting with the use of one or more counting bags.

Figure 6:
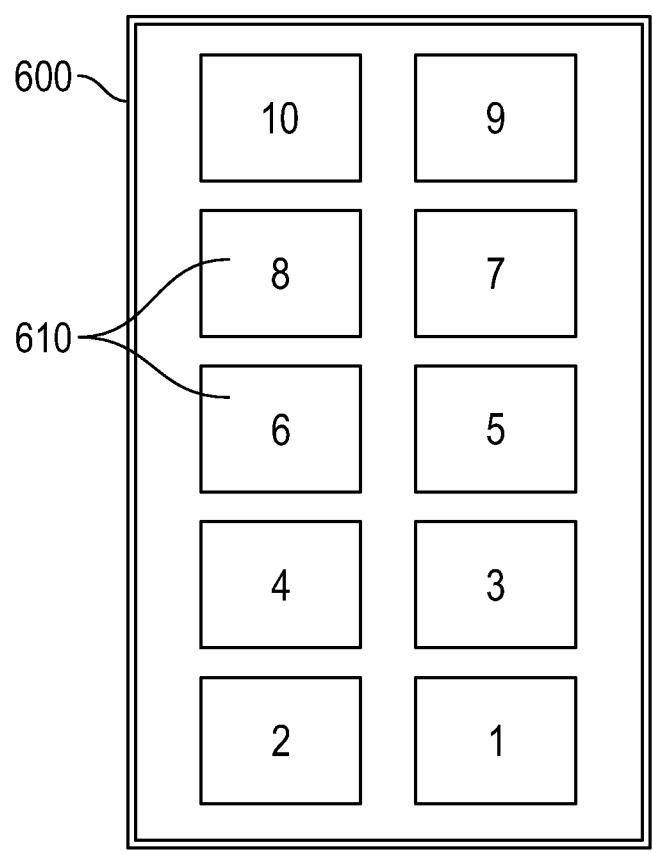
FIG. 6 is a schematic diagram depicting a protocol for counting surgical items, according to some example embodiments.

In some situations, medical personnel may employ a standardized procedure or protocol in counting surgical items using one or more counting bags. FIG. 6 depicts one such protocol for use in operating rooms. Items are placed in pockets 610 of a counting bag 600 in the order denoted by the numbers, for example, from bottom to top and from right to left. Thus, when the procedure is followed correctly, the first pocket filled is the bottom right corner pocket (pocket 1), and the last pocket filled is the top left corner pocket (pocket 10). According to other protocols, the counting bag 600 may be filled from top to bottom and from left to right. However, any other suitable protocol may be followed.

Figure 4:
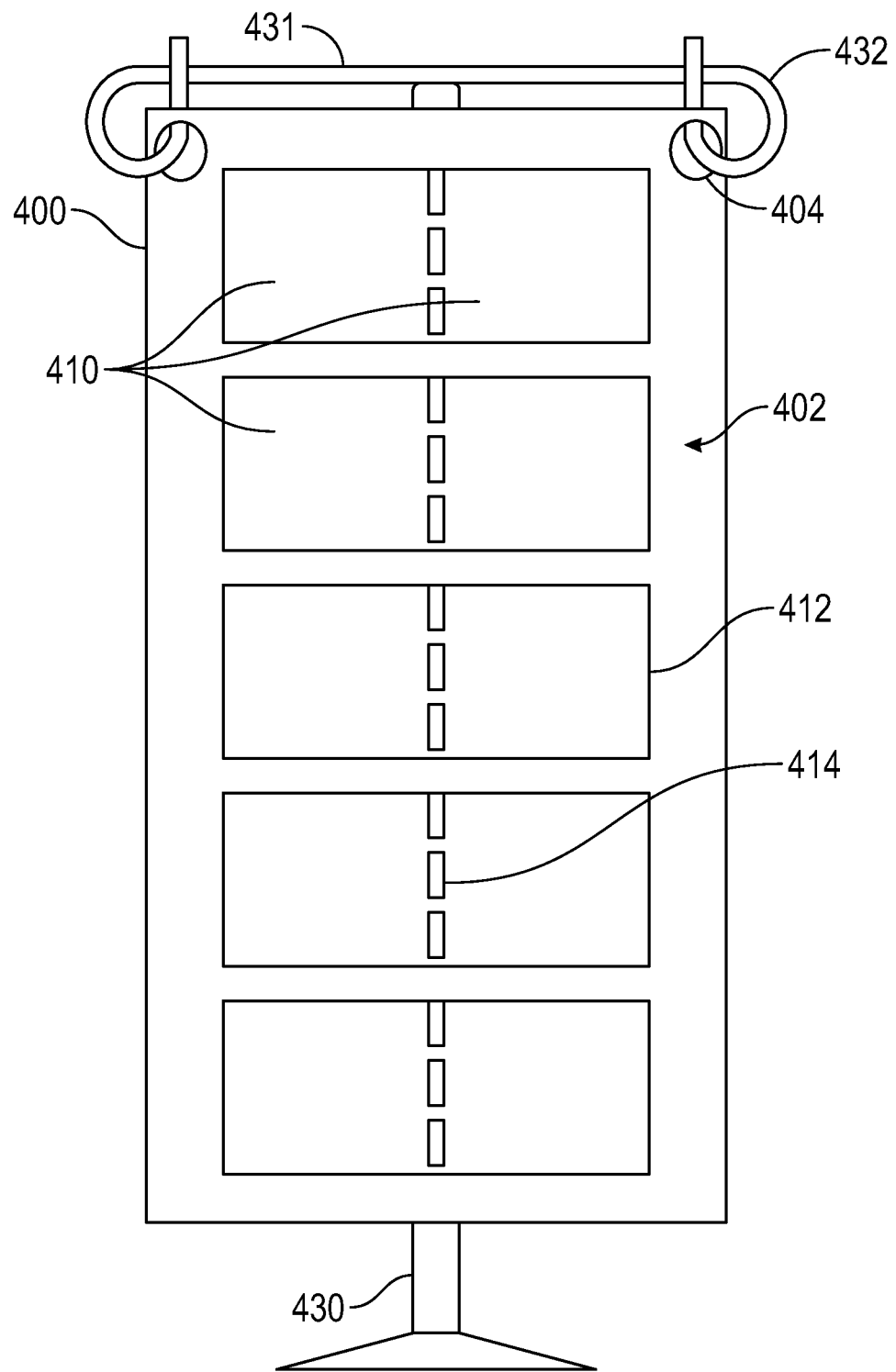
FIG. 4 is a schematic diagram depicting a container configured to receive surgical items for counting, according to some example embodiments.

FIG. 4 schematically depicts a counting bag 400 used in a medical procedure. The counting bag 400 comprises a backing 402 and plurality of pockets 410 or other compartments. In FIG. 4, the counting bag 400 includes ten pockets arranged in a rectangular array. As shown in FIG. 4, the ten pockets 410 are arranged in five rows, with each row including two of the pockets 410. Each row may, for example, include a larger pocket 412 formed between the backing 402 material and a front material, and the larger pocket 412 may be divided into two smaller pockets 410 with a seal 414 forming a seam in the larger pocket 412. However, the counting bag 400 may include any suitable number of pockets 410, and the pockets 410 may be configured in any suitable manner. For example, some or all of the pockets 410 may be separate compartments, some or all of the pockets 410 may be made from a single larger pocket (e.g., larger pocket 412) with each pocket 410 separated by a seal, or any suitable combination thereof. The counting bag 400 may be mounted to a stand, such as a pole 430 (e.g., an intravenous (IV) pole). The pole 430 may include a lateral mounting rod 431 comprising one or more (e.g., two) hooks 432. The counting bag 400 may include one or more (e.g., two) openings 404 that allow the counting bag 400 to hang from the hooks 432. Although the counting bag 400 depicted in FIG. 4 is rectangular and includes ten rectangular pockets 410, the counting bag 400 and its pockets 410 may be of any suitable configuration.

The counting bag 400 may include (e.g., be made of) any suitable material. For example, the backing 402 of the counting bag 400 may be made of flexible material, such as polymer, plastic, silicone, nylon, rayon, any other suitable material, or any suitable combination thereof. As another example, the backing 402 of the counting bag 400 may be comprised of a more rigid material, such as a rigid plastic, polymer, metal, any other suitable material, or any suitable combination thereof. The backing 402 of the counting bag 400 may be transparent, translucent, opaque, colored, or any suitable combination thereof. For example, the backing 402 may be opaque blue. An opaque and colored backing 402 (e.g., opaque blue) may make the counting bag 400 easier to be individually identified among multiple counting bags (e.g., where multiple counting bags are layered in front of each other on the same pole 430, or where multiple poles (e.g., pole 430) are layered in front of each other), and may provide a contrasting background against which surgical textiles stand out. The pockets 410 may be made of the same or different material as the backing 402. For example, the pockets 410 may be made of a flexible plastic, silicone, or polymer material. Pockets 410 made of flexible material may provide the benefit of allowing surgical textiles to be easily placed therein. Pockets 410 may also be transparent or opaque. In some example embodiments, one or more pockets 410 are transparent to allow for easy visualization and counting of surgical items.

Although the counting bag 400 depicted in FIG. 4 is rectangular and includes ten rectangular pockets 410, the counting bag 400 may be of any suitable configuration. For example, the backing 402 of the counting bag 400 may be rectangular, substantially square-shaped, oval, triangular, or any suitable shape. The counting bag 400 need not have ten pockets 410 as depicted in FIG. 4 and may include any suitable number of pockets 410. For example, the counting bag may include 2, 3, 4, 5, 6, 7, 8, 9, 10, 11, 12, 13, 14, 15, 16, 17, 18, 19, 20, or any suitable number of pockets 410. Although FIG. 4 depicts the counting bag 400 configured to hang from the pole 430, the counting bag 400 may be mounted in any suitable manner. For example, the counting bag 400 may have one or more openings 404 or any other suitable attachment mechanism in any suitable location. For example, a counting bag may be configured to be mounted to hooks on a wall, or mounted on hooks or mounting rods configured to be placed over the top or a door or cabinet. As another example, the counting bag 400 may be affixed to a wall with adhesive or other suitable fasteners. Further, the counting bag 400 need not be sized to fit the dimensions of the pole (e.g., an IV pole), and the counting bag 400, its pockets 410, or both, may be sized differently from other counting bags, their pockets, or both, to accommodate different types of surgical items, such as differently sized surgical textiles.

Figure 5:
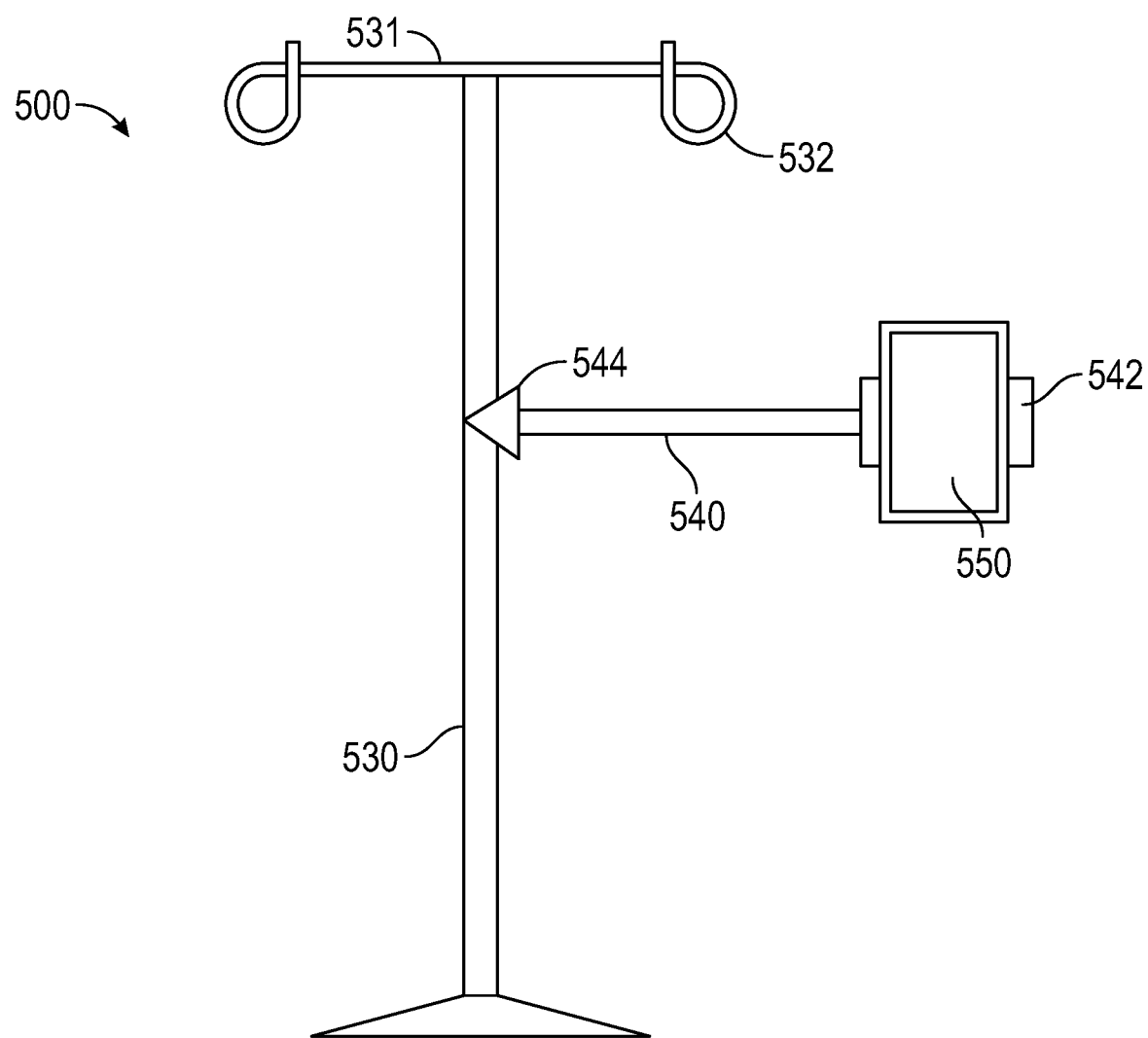
FIG. 5 is a schematic diagram depicting a mounting structure configured to hold an imaging device, according to some example embodiments.

In some example embodiments, the pole 430 may also include a mount for mounting an imaging device. One or more imaging devices may be used to generate one or more images for use in various components (e.g., operations) of methods for tracking surgical items, including the determining of the first count, the determining of the second count, or both. In particular, one or more imaging devices mounted to the pole 430 to which the counting bag 400 is mounted may be used in the determining of the second count of surgical items in the counting bag 400. For example, a mount for an imaging device may make the taking (e.g., capturing) of an image of the counting bag 400 easier for a user, so that the user does not have to hold the imaging device while taking the image. One or more mounts may be fixedly attached to the pole 430 or may be removably secured to the pole 430. Furthermore, a mount may be adjustable along the pole 430 (e.g., configured to slide vertically up and down the pole 430), rotationally adjustable around the pole 430 (e.g., adjustable to a left side or right side of the pole 430), or both. FIG. 5 schematically depicts an example embodiment of a counting bag stand 500, comprising a mount 540 attached to a pole 530 configured to hold a mobile device 550 (e.g., a tablet or a smartphone). In the example embodiment shown, the mount 540 includes a grip 542 configured to securely and releasably hold the mobile device 550. The grip 542 may hold the mobile device 550 using any suitable mechanism, for example, via a friction fit between the mount 540 and the mobile device 550, an adjustable clamp, a snap fit with mating parts on the mount 540 and on the mobile device 550, one or more magnets, a removable adhesive layer attached to the mount 540 or mobile device 550, or any suitable combination thereof. In the example embodiment shown, the mount 540 is secured to the pole 530 by an attachment mechanism 544. The attachment mechanism 544 may include any suitable attachment mechanism, such as a clamp, a clasp, a hinge, threads, one or more fasteners (e.g., mechanical fasteners, adhesive, both), or any suitable combination thereof. For example, the attachment mechanism 544 may include an adjustable clamp (e.g., adjustable jaws) or an expandable sleeve or other insert (e.g., inflatable, foam, etc.) configured to attach to, and adjust to, the dimensions of the pole 530. In some example embodiments, the attachment mechanism 544 includes one or more fasteners configured to couple the mount 540 to the pole 530 (e.g., a screw or bolt inserted through the mount 540 and through an opening in the pole 530, and secured with a nut, other threaded backing, or other fastener backing). Although the mount 540 in FIG. 5 is depicted as extending horizontally from the pole 530, the mount 540 may extend at any suitable angle such that the camera of the mobile device 550 can be positioned to capture an image of a counting bag (e.g., counting bag 400) mounted on the pole 530. Further, the mount 540 may be secured to any suitable portion of the counting bag stand 500. For example, the mount 540 may be secured to the pole 530, a mounting rod 531, or hooks 532 of the counting bag stand 500. Further, the mount 540 may have any suitable configuration. The mount 540 may be substantially straight, or the mount 540 may include a curved configuration. Further, the mount 540 may be adjustable in length, angularly adjustable (e.g., adjustable in the angle between the mount 540 and the pole 530), such as with a gooseneck structure, or any suitable combination thereof This may provide the benefit of allowing the user to adjust the positioning of the mount 540 according to the specific needs of the user or the procedure at hand.

Example Computational Techniques for Tracking Surgical Items

Figure 7:
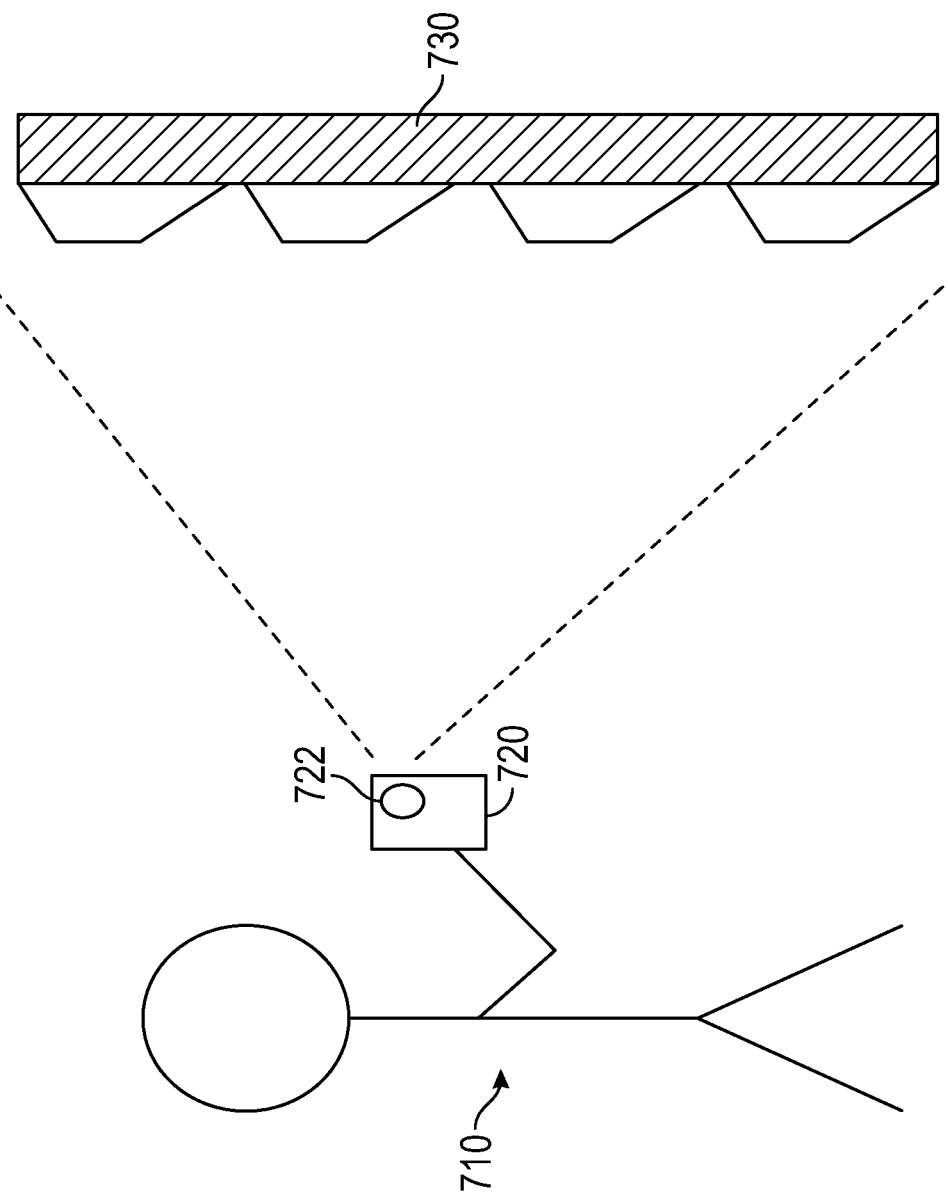
FIG. 7 is a schematic diagram depicting a user operating a mobile device to obtain an image of a container configured to receive surgical items, according to some example embodiments.

In some example embodiments, one or more computational techniques are used to identify, count, or both, surgical items that may have been placed into one or more counting bags (e.g., counting bag 400). Using one or more of such computational techniques in conjunction with one or more counting bags may be desirable to automate and streamline the process of surgical item accounting, and may improve the accuracy of one or more counts and thus compliance with the protocol for using the one or more counting bags. For example, one or more images of the counting bag 400 may be taken, and one or more computational techniques may be used to identify and count any surgical textiles in the counting bag 400 (e.g., using computer vision, machine learning, or deep learning, as described elsewhere herein). For example, a user may take an image of the counting bag 400 using an imaging system, such as an imaging system of the mobile device 550 (e.g., a mobile computing device). FIG. 7 schematically depicts a user 710 taking an image of a counting bag 730 using a mobile device 720. As shown in FIG. 7, the user 710 may position an imaging system in the example form of the mobile device 720 with a camera 722, such that the counting bag 730 is in the field of view of the camera 722, as depicted by the dashed lines in FIG. 7. One or more images generated by the camera 722 of the mobile device 720 may be analyzed using one or more computational techniques described herein. Although FIG. 7 depicts the user 710 holding the mobile device 720 in front of the counting bag 730 to generate an image, the imaging system (e.g., the mobile device 720) may be positioned relative to the counting bag 730 in any suitable manner, such as via a mount (e.g., mount 540 shown in FIG. 5) that is proximate the counting bag 730, or directly on the counting bag 730 angled toward the pockets (e.g., pockets 410) of the counting bag 730.

Example Models of Tracking Algorithms

Figure 8:
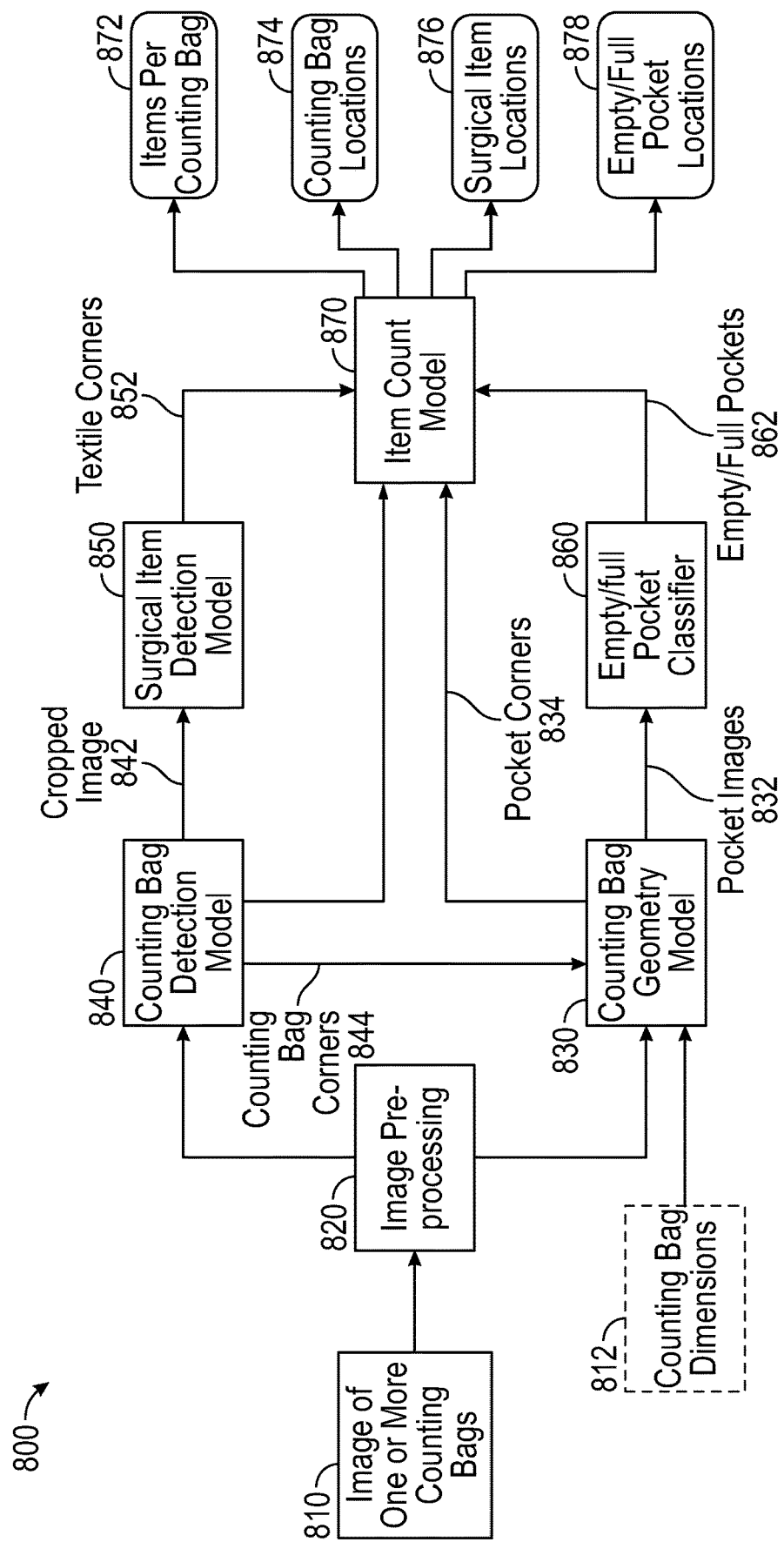
FIG. 8 is a schematic block diagram depicting components of a method of accounting for surgical items, according to some example embodiments.

FIG. 8 schematically depicts a method, according to some example embodiments, and shows example relations and data flows among various trained models and other possible components of a method 800 (e.g., a tracking algorithm) used to track surgical items placed in one or more counting bags (e.g., counting bag 400). Each model included in the method 800 may use machine learning, deep learning, or both, to accomplish its sub-goal. The algorithms in each model of the method 800 may be combined (e.g., in a unique manner) to arrive at an accurate accounting of surgical items in the one or more counting bags, as well as provide additional information to users. In some example embodiments, methods of tracking surgical items rely on two or more independent counting approaches, as well as one or more error reducing techniques, to arrive at a robust method of counting surgical items. Although the method 800 (e.g., considered as an overall tracking algorithm) described with reference to FIG. 8 is described in terms of a counting bag, the method 800 may be employed to count items (e.g., surgical items) configured or contained in any suitable manner. Further, the steps of the method 800 laid out below need not be performed in the order they are described or depicted in the flowchart shown in FIG. 8, and may be performed in any suitable order.

As depicted in FIG. 8, an input of the method 800 is an image of one or more counting bags (810). An image of one or more counting bags 810 may be obtained in any suitable manner, using any suitable imaging device. In some example embodiments, a user obtains an image of the counting bag 730 using the camera 722 on the mobile device 720 (e.g., a mobile phone or tablet). However, any one or more of various imaging systems may be used to obtain the input image, such as a digital camera, a camera on a computer, a video camera, etc. The image may then be received by a processor. The image may be pre-processed 820 for subsequent analysis. Pre-processing of the image may involve, for example, brightness normalization, contrast correction, reduction in the image size to a dimension suitable for processing by one or more deep learning or computer vision models, or any suitable combination thereof. The determining of a count (e.g., first count, second count, further count, or any suitable combination thereof) of surgical items in an imaged counting bag (e.g., counting bag 400 or 730) may include analyzing an image with one or more of various computational techniques, such as a counting bag detection model 840 for detecting presence of the counting bag in the image, a counting bag geometry model 830 to encode geometrical features (e.g., dimensions and other features of the counting bag and its one or more pockets within the counting bag), a surgical item detection model 850 for detecting the presence of any items in the counting bag, an empty/full pocket classifier model 860 for determining presence or absence of a surgical item (e.g., in general or of a specific type) in each pocket, or an item count model 870 for synthesizing information about surgical items in the imaged counting bag, providing a count of surgical items in the imaged counting bag, or both. In some example embodiments, after any pre-processing operations, the method 800 utilizes two or more pathways of item counting. For example, one pathway may be based on directly detecting surgical items in the counting bag, and one pathway may be based on identifying pockets in the counting bag and classifying the pockets as empty or full. The method 800 may then combine the results of the multiple counting pathways and may employ one or more error detection algorithms to arrive at a final accounting of surgical items.

The counting bag detection model 840 may receive the pre-processed image, or alternatively, an unprocessed image, of the one or more counting bags for analysis. The counting bag detection model 840 may identify the presence of at least one counting bag in the image, based at least in part on one or more trained machine learning or deep learning models. Examples of suitable object detection models include Faster region-based convolutional neural networks (R-CNN), single short detectors (SSD), and region-based fully convolutional networks (R-FCN), which may achieve high performance on object detection tasks. The counting bag detection model 840 may also utilize one or more of such trained models to identify the location of each counting bag in the image, identify or count 844 one or more edges, corners, or both, of the counting bag, or any suitable combination thereof. For example, as shown in the example graphical user interfaces shown in FIGS. 9 and 10, the counting bag detection model 840 may detect the presence of a counting bag 910 and indicate the location of the counting bag 910, one or more boundaries of the counting bag 910, or both, in a displayed image (e.g., indicated with a corresponding bounding box). In some example embodiments, the counting bag detection model 840 may crop the counting bag image according the identification of the counting bag (e.g., to substantially isolate the portion of the image corresponding to the identified counting bag), and output the cropped counting bag image 842 for later use.

The counting bag geometry model 830 may encode the geometrical information about one or more counting bags, such as the vertical and horizontal dimensions of a counting bag (e.g., counting bag 400 or 730), the locations of its pockets (e.g., pockets 410), or both, to help identify specific geometrical features of the identified counting bag. Counting bag dimensions 812 (e.g., with or without other geometrical information) encoded in the counting bag geometry model 830 may, for example, depend on the make (e.g., brand or manufacturer), the model, or both, of the counting bag, and may be pre-encoded (e.g., manually entered as associated with a particular make or model of counting bag) or learned from training data. In some example embodiments, the counting bag geometry model 830 may receive one or more inputs, such as locations of counting bag corners 814 or edges, with or without any other suitable information that may be helpful in identifying the geometry of the counting bag, analyzing the geometry of the counting bag, or both. In some example embodiments, the counting bag geometry is identified based at least in part on knowledge of the make of counting bag, which may be entered by a user as user input (e.g., through a user interface on a mobile application), identified via scanning an identifier code (e.g., barcode, QR code, etc.) on the counting bag, its packaging, or identified by recognizing the make of the counting bag directly from the image of the counting bag (e.g., based on optical character recognition of the label, characteristic color features, characteristic geometrical features, or any suitable combination thereof). For example, a user may input the make of counting bag, and the geometry model may use known information to aid in determining geometrical information for the counting bag. As another example, the user may manually identify the bounds of the counting bag, its pockets, or both, on a mobile device by applying reference markers or resizing one or more virtual outlines for defining the counting bag, its pockets, or both. The counting bag geometry model may, use homography or one or more other perspective transforms to automatically identify the location of the pockets of the counting. Based on these locations, the counting bag geometry model 830 crops the images of each counting bag pocket for receipt by the empty/full pocket classifier model 860. Accordingly, the counting bag geometry model 830 may provide pocket images 832 (e.g., identification of portions of the image corresponding to counting bag pockets, cropped image segments, or any suitable combination thereof), which may also contain information about the location of the pockets, their pocket corners 834, or both. For example, as shown in the example graphical user interface shown in FIG. 9 and, the counting bag geometry model 830 may detect the location of the counting bag, the shape of the counting bag's pockets, or both, and indicate the pockets of the counting bag (e.g., pockets 920A-920C) in a displayed image, with the pockets indicated by corresponding bounding boxes.

As noted above, there are multiple example embodiments (e.g., variations) of the method 800 for tracking (e.g., by counting) surgical items. In some example embodiments, the surgical item detection model 850 uses a deep learning algorithm or other suitable artificial intelligence model to identify each surgical item (e.g., each surgical textile) and the location of the surgical item in a cropped counting bag image 842, as generated by the counting bag detection model 840. The deep learning algorithm employed in the surgical item detection model 850 may be trained on a dataset (e.g., a reference dataset or other training dataset) that represents a diverse array of counting bag images, each labelled with an identification of each surgical item in the image. The deep learning algorithm of the surgical item detection model 850 can thus identify, locate, or both, the surgical items (e.g., surgical textiles) in each counting bag in an image. The surgical item detection model 850 may generate data on the boundaries of each surgical item in a counting bag. In the case of surgical textiles, this may be performed by identifying the textile corners 852, for example. Thus, the surgical item detection model 850 may provide the location of all the detected surgical items within one or more counting bags, and enable determination of a count (e.g., the first count, the second count, a further count, or any suitable combination thereof) of surgical items in one or more counting bags.

Figure 9:
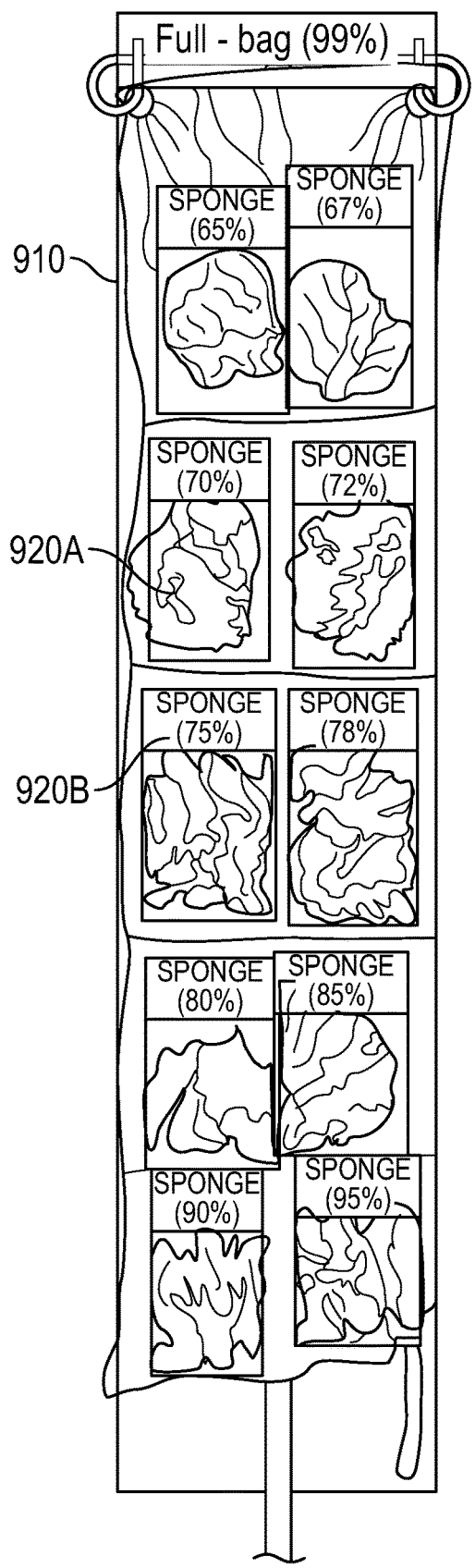
FIG. 9 is a diagram depicting a display of information generated by a method for tracking surgical items, according to some example embodiments.
Figure 10:
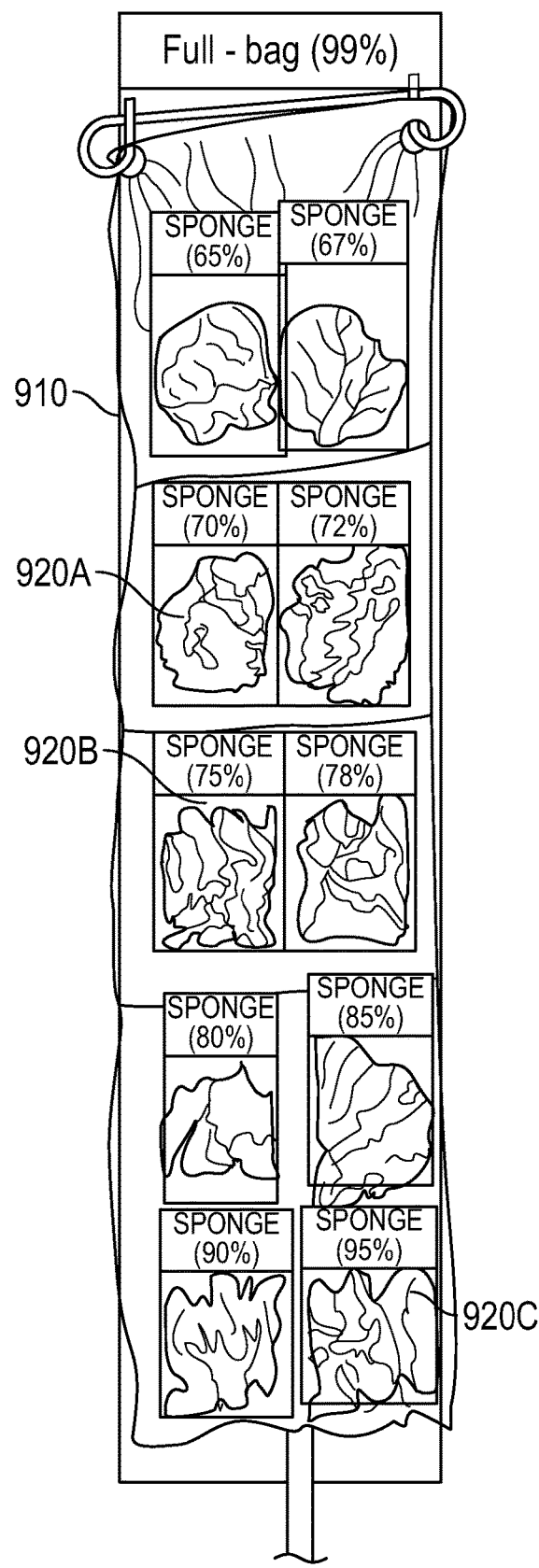
FIG. 10 is a diagram depicting a display of information generated by a method for tracking surgical items, according to some example embodiments.

In a certain example embodiments, the empty/full pocket classifier model 860 identifies whether each pocket is full or empty by analyzing an image of one or more counting bags in which the pockets have been identified by the counting bag geometry model 830. The cropped images of each pocket, as generated by the counting bag geometry model 830, are received by the empty/full pocket classifier model 860. The empty/full pocket classifier model 860 may use a deep learning algorithm, trained on a dataset of counting bag images labelled with empty/full pocket identifiers, to identify which pockets are empty and which pockets are full. Examples of suitable object classification networks include: Inception, ResNet, MobileNet, MnasNet, and EfficientNet, which may achieve high performance on object classification tasks. The output 862 of the empty/full pocket classifier model 860 includes information that indicates which pockets are empty and which pockets are full in one or more counting bags. The empty/full pocket classifier model 860 therefore enables determination of a count (e.g., the first count, the second count, a further count, or any suitable combination thereof) of surgical items in the one or more counting bags. FIGS. 9 and 10 depict example displays corresponding to the output 862 of the empty/full pocket classifier model 860. Based on a combination of information (e.g., from the surgical item detection model 850, the empty/full pocket classifier model 860, or both), a counting bag may be identified as a full counting bag (e.g., as shown in FIGS. 9 and 10), a partially full counting bag, or an empty counting bag. Furthermore, as shown in FIGS. 9 and 10, each pocket in an image of the counting bag may be individually identified as including a detected surgical item, such as a surgical sponge (e.g., pockets 920A and 920B), or as not including a detected surgical item (e.g., pocket 920C). The item count model 870 synthesizes the information generated by one or more of the previously described models to generate a variety of information about each analyzed image. For example, the item count model 870 may utilize prior information (e.g., determined counting bag geometry, surgical item detection, or both) and perform post-processing to arrive at or provide information on one or more surgical items (e.g., surgical textiles), one or more counting bags, or both, such as a final surgical item count, a counting bag location, one or more surgical item locations, one or more locations of empty pockets, and one or more locations of full pockets. As shown in FIG. 8, the item count model 870 may determine a total item count in each counting bag 872 in an image. For example, the item count model 870 may utilize information from one or more of the previously discussed models, such as the surgical item detection model 850, the empty/full pocket classifier model 860, or both, to determine a number of surgical items per counting bag 872. Furthermore, in some example embodiments, the item count model 870 combines information from one or more other models discussed above in various ways to determine an item count using a combination of multiple methods, and compare the counts arrived at using each method (e.g., verify counts against each other) to determine a final surgical item count.

For example, the item count model 870 may compare a first estimate of surgical items generated by the surgical item detection model 850, as described above, and a second estimate of surgical items generated by the empty/full pocket classifier model 860, as described above, to determine a surgical item count (e.g., the first count of surgical items or the second count of surgical items). In other words, the item count model 870 may compare the location of the detected surgical items within the counting bag as obtained using the two different types of deep learning models (e.g., by comparing the result of object detection by the surgical item detection model 850 to the result of object classification by the empty/full pocket classifier model 860). In some example embodiments, the item count model 870 receives information about the surgical items (e.g., surgical textiles) identified and detected by the surgical item detection model 850 to determine the first estimate of the surgical itemcount. The item count model 870 may use the information generated from the empty/full pocket classifier model 860 to generate a second estimate of the surgical item count. If the surgical item counts generated using both methods match, then the item count model 870 may use the matching counts as output in providing the count of items per counting bag 872. If the two counts do not match, the item count model 870 may respond by adopting a unique and novel approach of combining the outputs of the surgical item detection model 850 and the empty/full pocket classifier model 860, which may include utilizing knowledge of counting bag geometry, to correct the count and improve tracking (e.g., counting) accuracy, such as the approach described below.

The item count model 870 may also perform one or more methods of verifying one or more determinations of one or more item count estimates (e.g., if the counts based on the surgical item detection model 850 and the empty/full pocket classifier model 860 do not match). For example, the item count model 870 may take the total number of pockets identified or counted by the counting bag geometry model 830 and the total number of full or empty pockets identified or counted by the empty/full pocket classifier model 860 to determine how many surgical items (e.g., surgical textiles) are in the pockets of a counting bag (e.g., based on an assumption that there is only one surgical item in each full pocket). For example, if there are ten pockets identified by the counting bag geometry model 830, and one pocket is labeled as empty or nine pockets are labeled as full, then the item count model 870 can use this information to determine that the surgical item count is nine.

As shown in FIG. 8, additional useful information may be provided according to the method 800, based on information obtained from one or more of various models, in addition to determination of one or more counts of surgical items (e.g., a first or second count of surgical textiles in a counting bag). For example, the item count model 870 may provide counting bag locations 874 within an image, which may be useful for automatically highlighting all the count bags for visualization. As another example, the item count model 870 may provide locations of the identified or counted surgical items within the counting bag, such as an indication of which pockets of the counting bag contain a surgical item. This information may be used, for example, in one or more error correction methods, as described below. This information may also be useful to determine compliance with an item counting protocol (e.g., a protocol for counting surgical textiles). For example, if there are surgical textiles located in the top pockets of a counting bag, but the bottom pockets of the counting bag are empty, this may indicate that a user did not follow an approved counting protocol that requires filling the pockets of the counting bag from bottom to top. As another example of useful information, the item count model 870 may provide the locations of the empty and full pockets in the image of the counting bag. This may also be useful in determining compliance with the counting protocol and may serve as a verification of surgical item location or number of surgical items, highlight where the empty pockets are located in the counting bag for easy assessment by end users, or both.

Examples of Reducing Count Error by Combining Models

The method 800 (e.g., considered as an overall tracking algorithm for tracking surgical items) may adopt a unique and novel approach of combining multiple (e.g., several) models (e.g., deep learning models), such as the surgical item detection model 850 and the empty/full pocket classifier model 860, as well as utilizing the knowledge of counting bag geometry (e.g., from the counting bag geometry model 830), to improve tracking (e.g., counting) accuracy by removing or otherwise mitigating different types of errors. Two example methods for combining multiple models are described below for illustrative purposes.

In one example of combining multiple models to improve overall tracking accuracy, different models may be combined to correct or otherwise address errors that are common in item counting models. For example, a first type of error occurs when there is erroneous detection of the presence of a surgical item (i.e., a failure to detect the absence of a surgical item) that leads to a reduction in precision and an incorrect count of surgical items. A second type of error occurs when there is erroneous detection of the absence of a surgical item (i.e., failure to detect the presence of the surgical item), which leads to a reduction in recall rates and an incorrect count of surgical items.

In some example embodiments of the method 800, one or both of these types of errors are resolved with algorithmic reconciliation (e.g., algorithmic error correction). For example erroneous detection of presence or absence of surgical items may be addressed, for example, based at least in part on the assumption that the locations of the detected surgical items should align well with the locations of the detected pockets of the counting bag. Thus, one or more error correction models may identify and reject "identified" surgical items whose determined locations do not align with determined locations of counting bag pockets. For example, an error correction model may reject an identified surgical item based on the Euclidean distance between the center (e.g., centroid) of the detected surgical item and the center of the nearest counting bag pocket obtained from the geometry of the counting bag. That is, if the Euclidean distance between the center of the detected surgical item and the center of the nearest counting bag pocket is above a predetermined threshold, the error correction model may reject the identified surgical item as an error (e.g., as being erroneously identified) and accordingly not include this identification in a surgical item count. A correspondence between the remaining (non-rejected) identified surgical items and the counting bag pockets may be established based on the shortest Euclidean distance. That is, the error correction model may match a surgical item with a specific pocket by determining the closest identified pocket to each item (e.g., to verify that each surgical item corresponds to a pocket).

Once the correspondence is established, a comparison of the item detection results with the empty/full pocket classification results can be performed. For example, if the surgical item detection model 850 fails to identify a surgical item that is actually present (an instance of the second type of error described above), then the error can be corrected (e.g., by the error correction model) as the empty/full pocket classifier model 860 will identify the corresponding pocket as being full. Similarly, if the surgical item detection model 850 incorrectly identifies a surgical item within a pocket that is determined to be empty based on the empty/full classifier model 860, then this instance of detection can be rejected (e.g., by the error correction model).

One advantage of this algorithmic reconciliation approach is that it requires less training data to implement, and yet improves the performance of surgical item tracking compared to using any single model alone (e.g., using only the surgical item detection model 850 or using only the empty/full pocket classifier model 860).

In other example embodiments, multiple models may be combined to form a tracking ensemble network with the aim of improved overall tracking accuracy and reducing count errors. For example, in addition to using one or more training techniques such as those described in further detail below, an ensemble of surgical item detection networks may be trained with one or more suitable ensemble learning techniques (e.g., snapshot ensemble).

As an illustrative example, a penalty term may be added to the training of the surgical item detection model 850. Specifically, a loss function for the surgical item detection model 850 may be modified by adding a penalty term to automatically penalize detection of surgical items whose detected locations are not close (e.g., within a threshold distance) to their corresponding (e.g., nearest) pocket locations. The penalty term may, for example, be related to the distance between the corners of a detected surgical item (e.g., a surgical textile) and the corners of a counting bag pocket (e.g., as determined using the counting bag geometry model 830). Adding this penalty term directly to the training of the surgical item detection model 850 incorporates prior knowledge of the geometry of the counting bag (e.g., a sponge bag or other counting bag), and therefore effectively constrains the output of the surgical item detection model 850 to be close to the locations of the pockets of the counting bags (e.g., a grid of pockets). Additionally, end-to-end training of the surgical item detection model 850 may be performed to automatically take into account the counting bag's geometric information that was available during the training stage.

Furthermore in this example, an ensemble of multiple item detection networks of different types may be trained by varying the training data sets (e.g., datasets as further described below), such as randomly or in a K-fold manner, varying one or more hyper-parameters of the network (e.g., hyper-parameters such as depth, regularizer, penalty weight, or any suitable combination thereof), and performing an ensemble learning technique, such as snapshot ensemble. Similarly, an ensemble of multiple empty/full pocket classification networks of different types may be trained by varying the network architecture, varying the hyper-parameters of the network (e.g., as described above), or any suitable combination thereof.

Finally, results from all the different item detection networks and all the empty/full pocket classification networks may be used within a new stacked generalization network that may be referred to as a tracking ensemble network. The tracking ensemble network may be separately trained on a distinct set of validation data (e.g., a "hold-out" validation set) to learn how to best combine the predictions from each ensemble member. This separate training may help to improve the overall accuracy of the tracking (e.g., counting), as well as the accuracy of each surgical item prediction, each empty/full pocket prediction, or any suitable combination thereof. For example, the tracking ensemble network may evaluate a 10-dimensional occupancy vector (e.g., for a 10-pocket counting bag, where "1" denotes a full pocket and "0" denotes an empty pocket), and accordingly compute a loss function based on the dot product of the predicted occupancy vector (e.g., from each of the competing ensemble item detection networks and empty/full pocket classification networks) and the ground truth occupancy vector. Accordingly, when trained, the tracking ensemble network may weigh the prediction from each of the of the ensemble object detection and object classification networks so as to improve the overall accuracy of the method 800 (e.g., the overall tracking algorithm). Thus, although the grid penalty and ensemble approach described above may utilize more training data to implement, it may further improve the performance of the method 800.

Examples of Collecting Training Data

The successful training of one or more of the above-described models may be helped by collecting a representative dataset of training examples, and appropriately labeling the items (e.g., surgical items) in the dataset for the desired end goals. One or more of such datasets may, for example, be representative and include variations of counting bag images that would be expected to be found in an operating room or other setting where the trained model will be used. Thus, the datasets used to train models, such as one or more of the models in the method 800 (e.g., the tracking algorithm) described above, may include "good" images as well as "bad" images, as described below.

In some example embodiments of the model training discussed herein, good images may feature a counting bag from a correctly vertically oriented, full frontal view of the counting bag (e.g., not a side view, top view, or angled view), where no part of the bag is blocked by other objects. A good image may be in focus with sufficient resolution to read the text on the bag. Some imaging devices, such as mobile computing devices, may automatically take images with sufficient resolution by default. The counting bags in a good image may have intact pocket dividers (e.g., the seam dividing the pockets will not be ripped), and each pocket may contain either zero (0) or one (1) surgical item. One or more models of the method 800 may be trained on a set of good images, including images depicting variations that would be expected in the course of various medical procedures. For example, a training data set may include one or more of the variations in the counting bag, in the background or setting of the image, or both, as listed below in Table 1.

TABLE 1

| Counting Bag Variations | Background/Setting Variations |
| --- | --- |
| Distance between the counting bag and the imaging system. | Hospital setting. |
| Number of surgical items in a counting bag, including variations where the counting bag is not completely filled and has one or more empty pockets. | Lighting conditions. |
| Sequence of placing surgical items in a counting bag, including variations where the user fills the bag from the bottom up, from the top down, and random placements of surgical items within pockets of the counting bag. | Background features, such as the counting bag kept against a wall, a counting bag against a backdrop of a full operating room, a counting bag against a backdrop including various surgical instruments, etc. |
| Make or brand of counting bag. | Number of counting bags in an image (not including images where counting bags are overlapping each other). |
| Level of saturation of textiles within a counting bag. | |
| Item placement within each pocket, including variations where a textile holding ribbon is placed outside of a pocket, or rolled up around a textile. | |

In some example embodiments of the model training discussed herein, bad images may include images that are generally difficult to analyze, such as those in which the features of the counting bag or surgical items are difficult to detect (e.g., due to bad lighting, a blurry image, or both). Bad images are likely to be sent by users during practice, so it may be beneficial to train one or more models on variations of bad images to create one or more robust counting models resilient to imperfect images of counting bags. These bad images may also be used to help create "guardrail" algorithms that may warn users of the wrong way to use a counting bag, and may alert users when a bad image was taken to notify the user to provide a better image (e.g., a new image with better clarity). Examples of bad images include images where part of the bag is occluded by foreground objects (e.g., by a user's hand, rails, tubes, or any suitable combination thereof), images taken from an angle that makes it difficult to see the divider of the pocket or the seal of the pocket (e.g., between two or more surgical items), images of counting bags with a torn pocket divider or a torn pocket seal (e.g., where such a tear created a single large pocket where two individual pockets should be), images where there is more than one surgical item in a single pocket, images taken in errant lighting conditions or any other condition that may produce an image from which it is difficult for the algorithm to analyze and extract features, and images having combinations of any one or more of the above aspects.

Examples of Other Verifications for Counts

Figure 11:
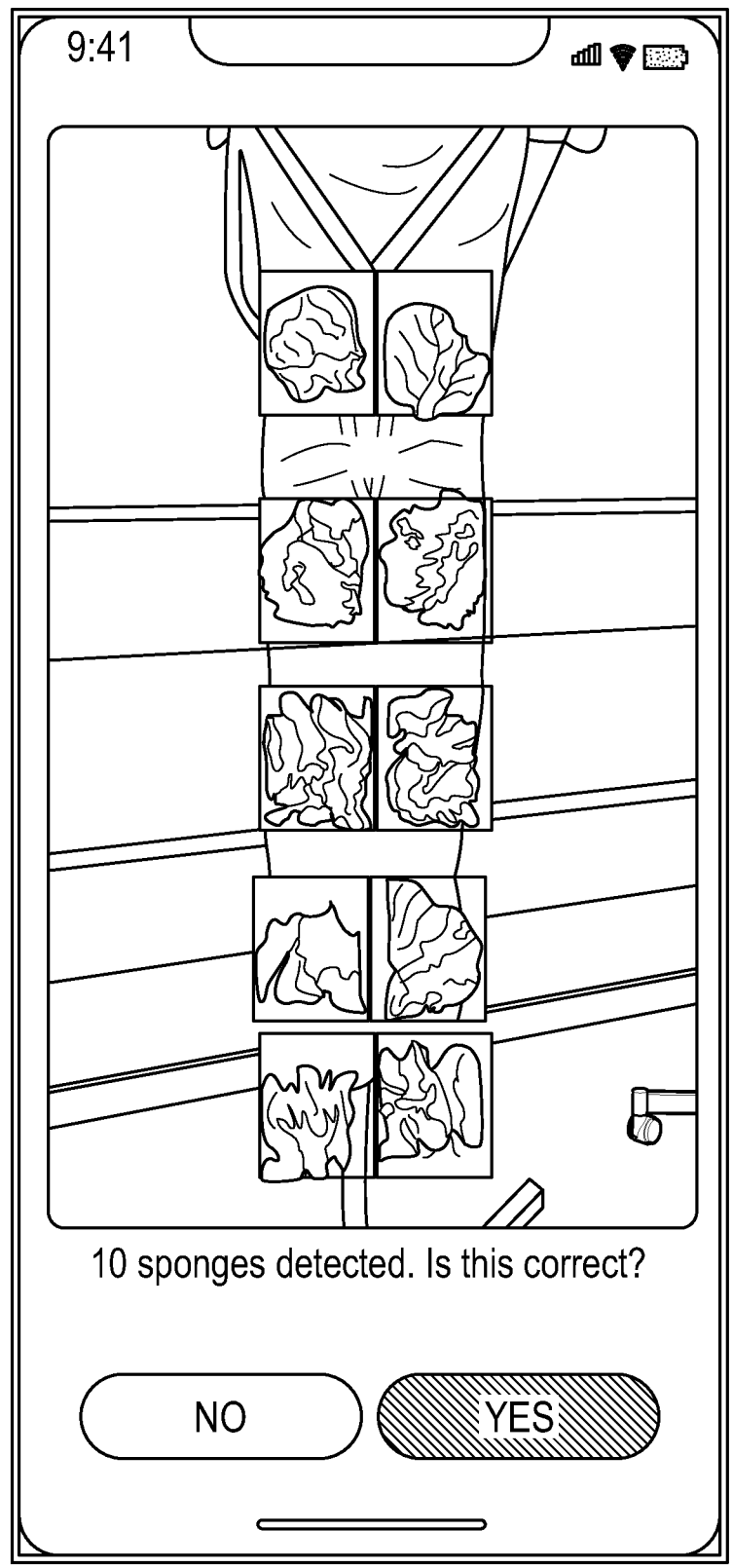
FIG. 11 is a diagram depicting a graphical user interface prompting user verification of a surgical textile accounting, according to some example embodiments.

In some example embodiments, the methods discussed herein may include one or more additional verification steps to provide a further check (e.g., an independent check) on the method 800. Providing one or more additional checking methods may improve the accuracy of surgical item accounting. Such additional methods may include prompting a user to manually verify a count of surgical items in a counting bag. Such additional methods may include requesting user verification of information generated by one or more of the various sub-models in the method 800. For example, one or more of such additional methods may include asking a user to verify that the method 800 has correctly identified a pocket, has correctly identified a counting bag, has correctly identified a full pocket, has correctly identified a surgical textile in a pocket, or any suitable combination thereof. For example, FIG. 11 depicts an example embodiment of a display on a mobile device, where the display is prompting a user to verify that the number of surgical items (e.g., surgical sponges) identified and counted by the method 800 is correct. As shown by the boxes surrounding the surgical items in FIG. 11, one or more of such additional methods may include displaying information to users indicating what the method 800 has identified as a surgical item.

In certain example embodiments, the methods discussed herein may include using weight information to verify a count of surgical items. For example, a pole to which a counting bag is mounted may be coupled to a scale. The scale coupled to the pole may sense a change in weight each time a surgical textile is placed into a counting bag, and accordingly count surgical items based on the number of weight increments sensed by the scale. The scale may be coupled to the pole in any suitable manner. For example, a mounting pole, the counting bag, or both, may be placed on the scale (e.g., with the mounting pole, the counting bag, or both, situated on top of the scale to measure changes in weight as items are added to the counting bag). Alternatively, the scale may take the example form of a strain gauge coupled to the mounting pole and coupled to the counting bag (e.g., with one end of the strain gauge hanging from the mounting pole and the counting bag hanging from the other end of the strain gauge). In some example embodiments, weight information may be generated from one or more surgical item collection containers, either instead of or in addition to weight information generated via one or more other methods. For example, a collection container may include a weight measurement system. As users remove surgical items from the collection container, the weight measurement system senses the weight decrement and determines that a surgical item textile has been removed from the collection container. A processor may log the number of weight decrements to determine a count of surgical items removed from the collection container, and thus a count of surgical items previously present in the collection container. Thus, use of one or more collection containers may provide an additional check on the count of surgical items (e.g., surgical textiles).

In various example embodiments, the methods discussed herein may include using time data from the removal of a surgical item from a collection container, and placement of a surgical item in a counting bag may provide an additional verification of a surgical item count. For example, a processor may generate a time stamp each time a weight measurement system senses removal of a surgical item from a collection container. Additionally, a processor may generate a time stamp each time a weight measurement system senses an addition of a surgical item to a counting bag. One or more processors may be configured to compare the time stamp of the removal of the surgical item from the collection container (e.g., a removal time stamp) and the time stamp of the addition of a surgical item to the counting bag (e.g., an addition time stamp) to provide a verification (e.g., an additional verification) on the count of surgical items. If the removal time stamp and the addition time stamp substantially align, that provides information indicating that the surgical textile count is correct.

Examples of Determining an Intermediate Count

In some example embodiments, the determining of the second count includes determining an intermediate count of surgical items during the course of a medical procedure (e.g., a surgical procedure). In alternative example embodiments, the determining of the second count includes determining a final count of surgical items after the medical procedure is completed. For example, the methods discussed herein (e.g., method 800) for tracking surgical items may include comparing the second count (e.g., as an intermediate count or as a final count) to the first count to account for surgical items at any point during the course of the medical procedure. Various example embodiments of such methods may include use of any one more of the above-described algorithms to determine the second count, whether it be an intermediate count or a final count.

The determining of an intermediate count of surgical items may include updating an index counter of surgical items. In some example embodiments, the updating of the index counter includes analyzing an image of a counting bag that includes one or more surgical items (e.g., surgical textiles) in one or more pockets of the counting bag. As counting bags are filled with surgical textiles by a user, one or more images of counting bags may be generated. One or more processors may receive the one or more images of counting bags, and one or more computational techniques may be used to process the one or more images to identify and count the surgical textiles in the one or more counting bags, such as one or more of the techniques described above.

Figure 13:
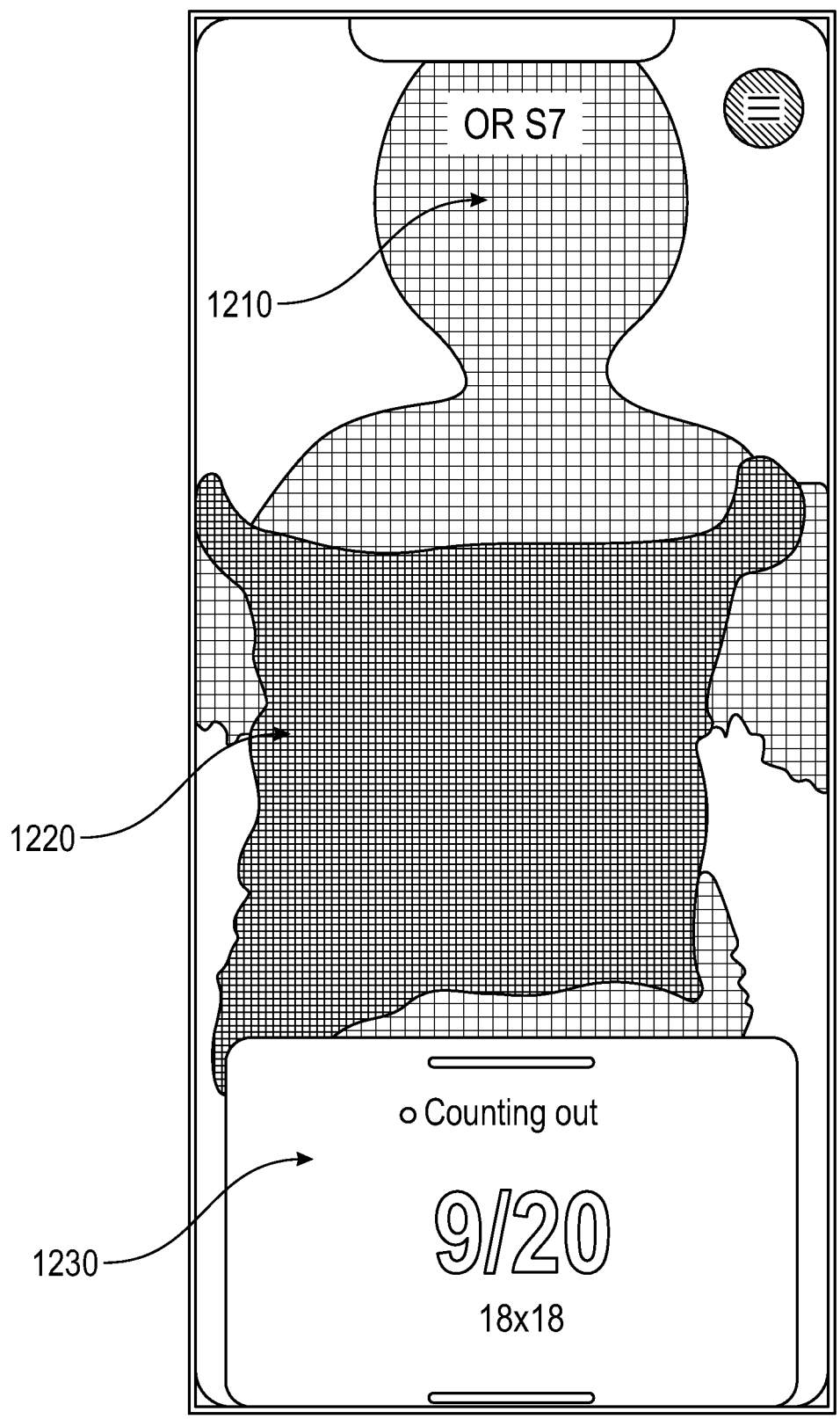
FIG. 13 is a diagram depicting a graphical user interface showing information related to tracking surgical items, according to some example embodiments.

In some example embodiments, instead of or in addition to analyzing an image of a counting bag comprising surgical items, the methods discussed herein include holding up a surgical item in a field of view of a camera. For example, a user may hold up a surgical item (e.g., a surgical textile, such a surgical sponge) to a camera, and the camera may generate an image that depicts the surgical item. The image may be received and analyzed by one or more processors configured to detect the presence of a surgical item depicted within an image. The image of the surgical item may be used to track surgical items. For example, an index counter may be updated each time a surgical item is held up to the camera and identified by the one or more processors. In some example embodiments, the index counter updated using image analysis of surgical items held up to the camera may be compared to a further index counter updated using image analysis of surgical items in one or more counting bags (e.g., as described above) to verify the index count of surgical items. FIG. 13 depicts an example of a graphical user interface in which an image of an individual surgical item (e.g., a surgical textile) is obtained and analyzed to update the count of such surgical items. Specifically, a user 1210 is holding up a surgical textile 1220 in front of a camera which captures an image (e.g., a depth image, color image, or both), so that one or more processing components (e.g., processors) can identify the surgical textile 1220 in the image and include the imaged surgical textile 1220 in an item count 1230. Example systems and methods for accomplishing the above are described in further detail in U.S. Pat. No. 8,897,523 and U.S. Patent Publication No. 2017/0186160, each of which is incorporated herein in its entirety by this reference. Furthermore, as described below, one or more methods of estimating an amount of blood loss may be used in conjunction with one or more of the methods discussed herein for tracking surgical items, and accordingly may include a user holding one or more surgical items up to a camera for imaging.

The determining of an intermediate count of surgical items may further include updating the index counter with the number of surgical textiles in one or more containers (e.g., in one or more counting bags) as the containers are filled and imaged. This process may be repeated throughout the medical procedure to continuously update the index counter and maintain a running count of surgical items (e.g., surgical textiles) that have been loaded into the one or more containers at any given time point. In some example embodiments, it may be desirable to compare the intermediate count (e.g., the current value of the index counter) to the first count of surgical items. For example, a user may want to know how many surgical items have been loaded into a set of counting bags and accounted for, and how many surgical items are currently either in use or unaccounted for.

Figure 14:
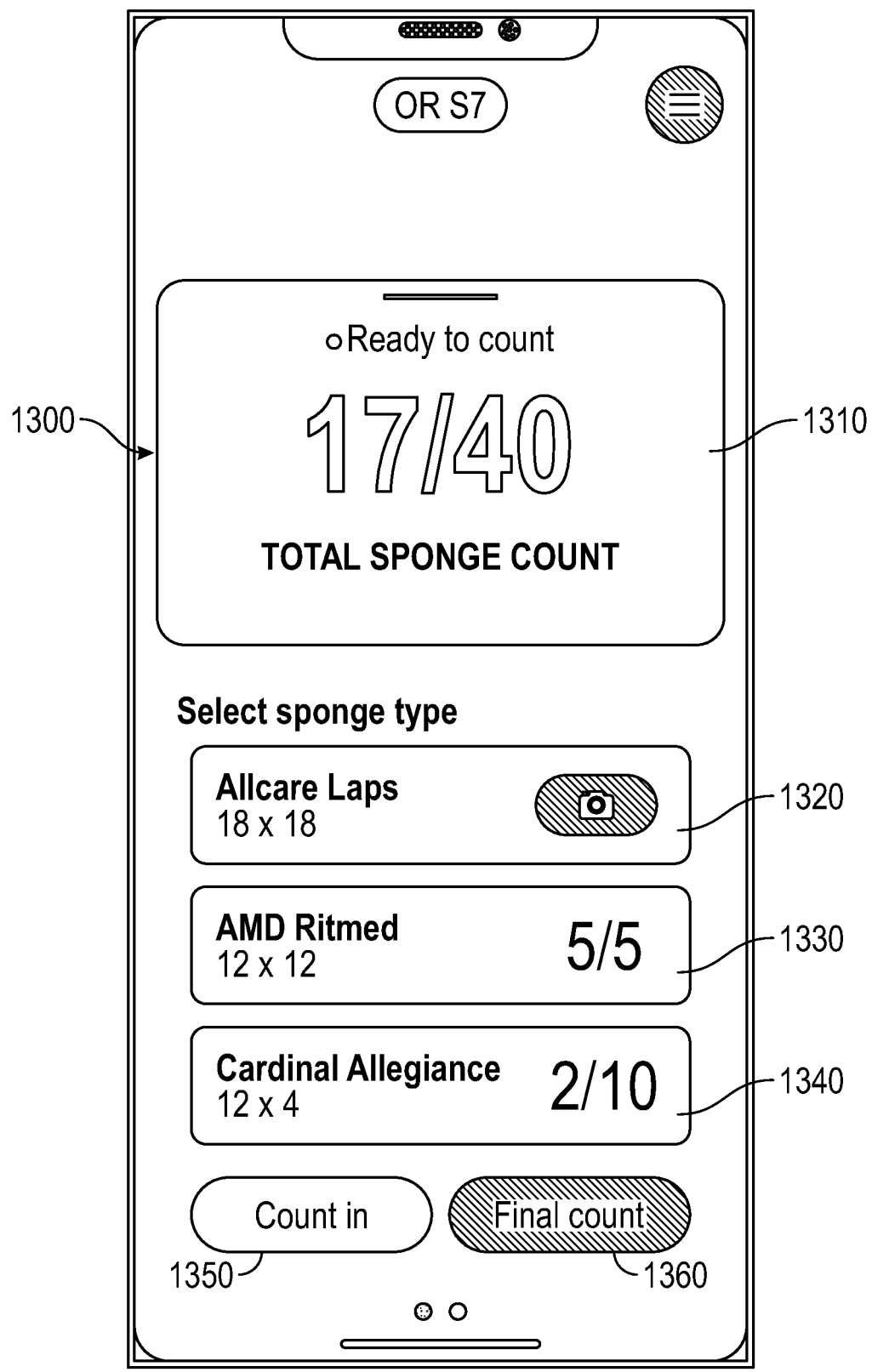
FIG. 14 is a diagram depicting a graphical user interface showing information related to tracking surgical items at an intermediate time point during a surgical procedure, according to some example embodiments.

Certain example embodiments of the methods discussed herein include displaying or otherwise providing the intermediate count to a user at any suitable point during the medical procedure. Displaying the intermediate count may provide a user with useful information regarding how many surgical textiles have been accounted for at a particular time point. FIG. 14 depicts an example of a graphical user interface 1300 that displays information regarding an intermediate count. Box 1310 of the screen in FIG. 14 shows a total number of surgical sponges accounted for (e.g., "17") compared to the first count of sponges (e.g., "40"). Further, information related to the types (e.g., brand, size, functional type, etc.) of surgical sponges accounted for is displayed in boxes 1320, 1330, and 1340. The graphical user interface 1300 also provides features that allow the user to update the first count by selecting a "count in" icon 1350 and to determine a final count by selecting a final count icon 1360.

Examples of Detecting Duplicate Images

Some example embodiments of the methods discussed herein may further include determining whether a particular counting bag has been previously imaged and analyzed. Because a user may take images of multiple counting bags, multiple surgical items, or both, there is a possibility that an individual counting bag, an individual surgical item, or both, may be inadvertently imaged multiple times, which may lead to an inaccurate count of surgical items. To counteract these consequences of inadvertent duplicate imaging, one or more of the images may be analyzed to determine a measure of likelihood that the image depicts the same counting bag as another image. Examples of methods for determining whether a counting bag has already been accounted for may include measuring or otherwise determining a likelihood that a first image and a second image have image regions that each depict at least a portion of the same textile (e.g., in the same counting bag). Example methods for measuring the likelihood that the first and second images have image regions that each depict at least a portion of the same textile are described in detail in PCT Application No. PCT/US2017/068234, which is incorporated herein in its entirety by reference. Example methods for determining whether an image of a particular counting bag has already been received and analyzed may include receiving a first image in which a first image region depicts a counting bag, receiving a second image in which a second image region depicts a counting bag, and defining at least one classification feature at least partially based on a first aspect of the first image, a second aspect of the second image, or both. Such example methods may further include measuring a likelihood that the first and second image regions depict at least a portion of the same counting bag, where the measuring of the likelihood is based at least in part on the classification feature, such as by using a machine learning classification algorithm. Such example methods may include comparing the measured likelihood of duplicate imaging to a predetermined threshold, where the threshold is or includes a cutoff for classifying an image pair as "not duplicate" or as "potentially duplicate." A similar process may be performed for measuring a likelihood that a first image region and a second image region depict at least a portion of the same surgical textile or other surgical item.

If the method 800 determines that the likelihood of duplicate imaging is above the predetermined threshold, follow-up actions may be prompted. For example, although generally each new image of a counting bag or a surgical item obtained may correspond to an increase in the count of surgical items (e.g., surgical items that have been extracted from the patient or from the sterile area of the surgical procedure for a second count), the count may be adjusted based at least in part on the measured likelihood that the counting bag, the surgical item, or both, has been imaged more than once. The detection of a potential duplicate image of a surgical counting bag or surgical item may, for example, trigger a prompt to the user to confirm whether the counting bag, the surgical item, or both, has been imaged more than once. As another example, the detection of a potential duplicate image of a counting bag or surgical item may automatically withhold from incrementing the count of surgical items. Example methods of determining whether a counting bag has already been imaged may comprise the use of identification tags. For example, counting bags, surgical items, or both, may include scannable tags (e.g. RFID tags or barcodes), and a scanner may be used to determine whether a counting bag has already been imaged. A scanner may be a separate scanning device or may be incorporated into a mobile device. One or more example methods involving scanning tags or barcodes may be employed instead of or in addition to one or more techniques involving image analysis.

Examples of Determining a Final Count

The second count may, in some example embodiments, include a final count of surgical items. For example, example embodiments of the methods discussed herein may include determining a final count of surgical items, and comparing the final count to the first count of surgical items. The final count may be differentiated from the intermediate count, for example, based on the final account referring to the count of surgical items that are accounted for at a time point in a procedure when surgical items are no longer being introduced or used. For example, the final count may be taken at the end of the medical procedure. The end of the medical procedure may be indicated in any suitable manner. For example, the end of the medical procedure may be after closing of the surgical site, after all operational procedures are performed on a patient with the exception of closing the surgical site, once the patient is ready to be removed from the operating room, or any other time point that is suitable to use as the final indication. In some example embodiments, the determining of the final count may be prompted by a user. For example, a mobile application or other computational program may allow the user to indicate when the final count is to be indicated (e.g., selection of the final count icon 1360 in FIG. 14). In some example embodiments, the mobile application may prompt the user to verify that a count of surgical items should be labeled as the final count based on a certain indication. For example, when the index counter reaches the value of the first count, the mobile application may prompt the user to confirm whether the current value of the index counter should be indicated as the final count. In other example embodiments, the mobile application may ask the user to indicate whether an index counter should be indicated as a final count after a certain amount of time has elapsed.

Examples of Providing a Notification Based on the First Count, the Second Count, or Both Various example embodiments of the methods discussed herein for tracking surgical items may include comparing the first count of surgical items to the second count of surgical items. For example, some example embodiments of such methods of tracking surgical items include comparing an intermediate count (e.g., among one or more intermediate counts) to the first count, as described above. Certain example embodiments of such methods include comparing the final count to the first count to determine whether the first and final counts match, and accordingly whether all surgical items introduced into the operating room have been accounted for. The comparing of the final count to the first count can assist medical staff in confirming that all surgical textiles or other surgical items were accounted for, and not retained by or in the patient. Some example embodiments of such methods may include notifying a user of whether the first count matches the second count (e.g., the final count or an intermediate count). For example, certain example embodiments of such methods include displaying a summary report of surgical item counting measurements, wherein the first count, the second count, and an indication of whether the first count matches the second count, are displayed to one or more users.

Figure 15:
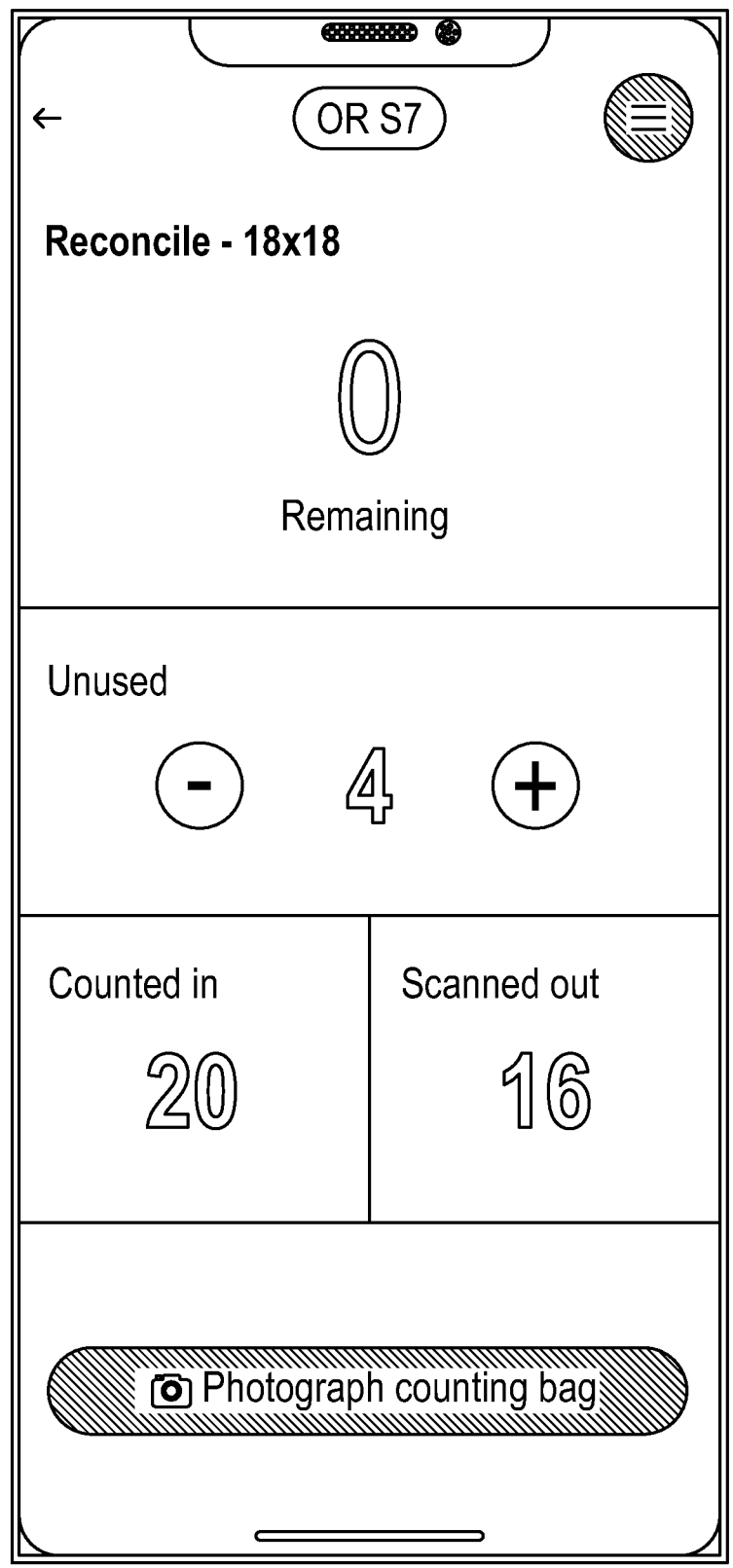
FIG. 15 is a diagram depicting a graphical user interface comprising a summary report of an accounting of surgical items, according to some example embodiments.

FIG. 15 depicts an example of a graphical user interface displaying a summary of surgical textile data. The screen in FIG. 15 shows the number of textiles "counted in" (e.g., introduced into an operating room), the number of textiles "scanned out" (e.g., imaged in a counting bag), and the number of unused textiles (e.g., introduced into the operating room but not yet imaged in the counting bag). In some implementations, unused surgical textiles are placed in one or more counting bags in the same way as used surgical textiles. In some other implementations, unused surgical textiles are accounted for using a different method, such as being identified in the one or more counting bags as unused and accordingly labelled as such on the display screen. In some example embodiments, the methods discussed herein include notifying a user (e.g. by providing a notification to the user) that the compared counts match. Such a notification may include a brief message indicating to the user that the counts match, or the notification may be symbolic. For example, the notification may include displaying a checkmark or equals sign or any other suitable symbol next to the first and final counts, displaying a color indication such as a screen turning a particular color (e.g., green) when the counts match, playing an audio indication that the first count and the final count match, some form of flashing or vibrating if the final counts match, or any suitable combination thereof. Furthermore, as described in further detail below with respect to FIG. 16, a summary report may be provided to one or more users for personal reference, for hospital records (e.g., accountability purposes), or both, and the summary report may indicate the first count and the final count, for each of one or more types of surgical items. For example, the summary may include or indicate a representation of the comparison between the first and second counts, such as the "reconcile" number shown in FIG. 15.

In certain example embodiments, the methods discussed herein include providing a notification to a user that the compared counts do not match. In situations where the final count of surgical items does not match the first count of surgical items, the notification may include an alert to the user. The alert may be in the example form of a display (e.g., on a mobile device) indicating to the user that there are one or more surgical items unaccounted for. The display may include any one or more of the elements described above in reference to the notification that the compared counts do match, except for aspects inconsistent with indicating that the compared counts do not match. In some example embodiments, the notifying of the user that the first and final counts of surgical items do not match includes providing a pre-determined protocol for proceeding in the event of a non-matching accounting. For example, the notifying of the user may include displaying (e.g., on the screen of a mobile device) steps of the predetermined protocol, providing accompanying audio cues, for both, regarding what to do when the first and final counts of surgical items do not match. Although medical personnel may be familiar with one or more protocols for how to precede in the event of an unaccounted for surgical item, the providing an additional presence (e.g., an additional instance of the protocol) that is unaffected by the potential unease of an unaccounted for surgical item may be beneficial in helping users comply with the protocol. This may lead to decreased instances of surgical items being retained in patients, better detection of retained surgical items when they do occur, more effective responses in the event of a retained surgical item, or any suitable combination thereof. In the event of unreconciled first and final counts, some example embodiments of the methods discussed herein may include automatically sending a notification to alert additional personnel, triggering a response protocol, or both. For example, unreconciled first and final counts may trigger a notification to hospital administrative staff, to a radiologist (e.g., to obtain pre-approval for generating an x-ray of the patient), to an X-ray technician, to additional medical personnel to help remedy the situation, or to any other suitable personnel.

If the first count and the final count do not match, some example embodiments of the methods discussed herein for accounting for surgical items may include executing a pre-determined protocol to determine whether there is a retained surgical item (e.g., retained in or by a patient). The executing of the pre-determine protocol may be done with the assistance of one or more computational tools, such as a device and a display to guide users through the protocol. The protocol may first include notifying all medical personnel present in the operating room of a potential retained surgical item. The protocol may then include re-counting all surgical items in the operating room and checking the room for surgical items that may have been misplaced. The recounting of surgical items may include operating one or more computational counting systems, using one or more manual counting methods, or any suitable combination thereof. Example of manual counting methods include re-counting the number of counting bags, recounting the number of surgical items in each counting bag, checking each pocket to determine whether there is more than one surgical item in a pocket, or any suitable combination thereof. The checking of the operating room for surgical items may include checking the trash (e.g., checking one or more trashcans), checking one or more collection containers, checking the area surrounding the patient, checking one or more counting bags for instances of multiple items placed in the same pocket, or any suitable combination thereof. If the first and final count still do not match after re-counting surgical items and checking for misplaced surgical items, the protocol may include taking an X-ray image or other internal image of the patient to detect any presence of a retained surgical item within the patient. The taking of the X-ray image may include alerting a radiologist of the need for the taking of the X-ray image and may require obtaining approval from the radiologist to proceed. The taking of the X-ray image may additionally or alternatively include notifying other suitable medical staff. The protocol may also include notifying hospital administration of other management personnel of an unreconciled surgical item count.

Examples of Additional Methods

The computational systems and methods (e.g., algorithms) described herein have broad applicability to affect a variety of improvements in medical procedures. Some example embodiments of such methods may include tracking user compliance, guiding a user through a counting protocol, tracking surgical item usage throughout a procedure, receiving patient and/or operating room information, triggering additional actions upon receipt of certain indications, or any suitable combination thereof, as described in detail below.

Certain example embodiments of the methods discussed herein comprise tracking compliance with one or more protocols. The tracking of user compliance may include tracking user compliance with a textile counting protocol for using counting bags. As described above, one or more pre-determined procedures may govern one or more desired methods of placing items in one or more counting bags. According to the applicable one or more protocols, operating room personnel may be instructed to fill the pockets of each counting bag from bottom to top, and right to left. In some situations, one or more algorithms developed according to one or more of the methods described above may be used to evaluate whether a user has complied with a bag filling protocol. Such an algorithm may receive one or more input images and determine compliance based on the one or more images. For example, a series of images taken over time may be analyzed to determine in what order the counting bag was filled. In other situations, video analysis may be used to identify and track the order in which the counting bag was filled. The algorithm may analyze the time-series of images or video to determine the order in which the user filled the pockets of the counting bag and evaluate the user's compliance with the applicable one or more protocols.

Some example embodiments of the methods discussed herein include providing a notification upon detecting non-compliance with a counting protocol. For example, such methods may include displaying an alert to the user as a reminder of the proper protocol, sending a notification to hospital administration staff, other hospital personnel, or both, indicating a misapplication of a textile counting procedure, or any suitable combination thereof. As another example, such methods may include triggering an alert for other medical personal to intervene in an incorrect filling procedure. For example, upon detecting a misplaced surgical item (e.g., a surgical item placed in a pocket of a counting bag in contradiction to the pre-determined procedure of the applicable protocol), such methods may notify a supervisor or peer to intervene in the bag-filling process.

Certain example embodiments of the methods discussed herein include prompting a user to enter their name in conjunction with use of a counting or tracking algorithm. A mobile application may prompt a user to input their name or other unique identifier, either before or after operating the application to take an image of a counting bag for processing. For example, the mobile application may prompt the user to scan his or her ID badge to provide such identification information. Compliance data may be paired with identification information to enhance user accountability. Pairing compliance information with user identification information may provide the benefit of allowing hospital administration to implement training or disciplinary protocols for users who are not following proper item counting procedures.

Various example embodiments of the methods discussed herein include guiding a user through a counting protocol (e.g., a textile counting protocol) using a counting bag. One or more computational techniques may be used to indicate to a user which pocket of the counting bag to fill next or identify a pocket that a user forgot to fill, for example, by presenting one or more visual cues, one or more audio cues, or any suitable combination thereof. For example, a display screen may provide a visual indication directing one or more users to the next pocket to be filled (e.g., by providing a box or circle around the pocket, displaying arrows as directional guidance, or both). Thus, such methods may direct a user through the protocol for filling the counting bag.

Some example embodiments of the methods discussed herein include providing one or more other kinds of tracking metrics for surgical items. Such methods may be used to gather information about a medical procedure at various time points throughout the medical procedure. For example, such methods may include tracking used versus unused surgical items. The tracking of used versus unused items may include a user manually separating or sorting items based on whether they are used or not. For example, a user may place used items in one container and unused items in a separate container. Various methods, such as one or more of the computational techniques described above, may be used to identify the used versus unused containers and count used and unused items. Such methods may include taking an image of a portion of an operating room with the used and unused containers, and one or more of the image analysis methods described herein may be used to extract information from the image. The identifying and counting of used versus unused items during the medical procedure may provide one or more useful metrics about the medical procedure. A single snapshot at a particular time point in a medical procedure (e.g., at the end of the medical procedure) may provide information about how many items were removed from their packaging versus how many items were actually used. A series of images taken throughout the medical procedure may be used to identify and count used versus unused items and may provide information about how items are used in that medical procedure over time.

Certain example embodiments of the methods discussed herein include receiving information related to the medical procedure. Such methods may allow users to input patient information (e.g., patient data), such as patient statistics or characteristics (e.g., height, weight, sex, age, etc.), the medical procedure to be performed, the expected length of the medical procedure, whether the medical procedure is scheduled or emergency, one or more pre-existing conditions, other pertinent information, or any suitable combination thereof. Such methods may include receiving, displaying, or both, various information about one or more environmental parameters, such as the which operating rooms are in use and which are available, whether certain equipment is available in a particular operating room, which medical personnel are currently working, other suitable parameters, or any suitable combination thereof.

Some example embodiments of the methods discussed herein include receiving information that may trigger an event or a protocol (e.g., one or more requests or initiations of one or more precautionary actions in response to determining that relatively high risk is present for one or more surgical items being retained in the patient). Such methods may comprise allowing a user to request additional items or equipment for use in the medical procedure. Such methods may include triggering a protocol upon receiving information about one or more of certain indications. It may be the case that one or more certain patient parameters combined with one or more of certain occurrences during the procedure indicate a high risk of a particular event taking place. For example, patients with a BMI in a certain range in combination with a threshold number of surgical items expected to be used (e.g., when the first count exceeds a predetermined number) during the medical procedure may indicate an increased risk of a retained surgical item. Therefore, such methods may include using patient data in combination with surgical item counting to trigger one or more additional protocols once a threshold number of surgical items are counted. Such a protocol may involve, for example, alerting an x-ray technician to prepare the appropriate equipment to take an X-ray image of the patient, providing a notification to a radiologist to obtain pre-approval to take the X-ray image of the patient, or both.

Certain example embodiments of the methods discussed herein include displaying or otherwise providing information related to the medical procedure. Such methods may include providing, displaying, or both, a summary report. The summary report may, for example, be stored as part of an electronic medical record of the patient, as evidence of compliance with one or more surgical item tracking protocols, or both. Any suitable information may be included in the summary report. As described above, information relating to one or more counts of surgical items, one or more comparisons of counts of surgical items, or both, may be displayed in the summary report. Additionally or alternatively, one or more images of individual surgical items, individual counting bags, or both, may be stored, displayed, or both, as a record (e.g., in the summary report). However, additional information about the medical procedure may also be displayed, such as the type of medical procedure, the length of the medical procedure, patient information, doctor information, hospital information, or any suitable combination thereof. Blood loss metrics may also be displayed. For example, where analysis of surgical textiles is used to monitor patient blood loss, a blood loss estimate may be displayed in the summary report. The summary report may include display of one or more symbolic indications of the outcome of the medical procedure. For example, a display may be a particular color where blood loss is in a given range (e.g., the display may be green when the blood lost is within a pre-determined range defined between pre-determined thresholds, and red when the blood lost is not with the pre-determined range). One or more summary reports may be generated at any suitable time point during the medical procedure. One or more summary reports may be displayed on a digital screen (e.g., a display screen of a mobile device, such as a phone or tablet), stored in memory (e.g., as part of an electronic medical record for the patient or for the hospital) and saved for later viewing, digitally sent to the patient or medical personnel, sent to a printer and printed, or any suitable combination thereof. FIG. 16 depicts an example of a summary report that includes information regarding compliance with a counting protocol, as well as additional information about the medical procedure performed. The summary report in FIG. 16 includes information regarding the case number, case location (e.g., which operating room was used), the start and end times of the medical procedure, the duration of the medical procedure, the number of surgical items (e.g., surgical textiles, denoted "sponges") counted, and the name of the person who performed the final count of surgical items. According to various example embodiments, summary reports may display any suitable information about the medical procedure, such as any information described herein.

Some example embodiments of the methods discussed herein provide one or more ways to enter an "emergency mode," in which some functionality of the method or system may be altered. For example, a textile counting algorithm (e.g., implemented via a mobile application) may allow a user to select the emergency mode, which may indicate that the counting protocol is no longer being followed. This may trigger one or more of various actions, such as halting the collection of item count data, refraining from tracking user compliance with a counting protocol, or alerting hospital staff to the emergency.

Figure 12:
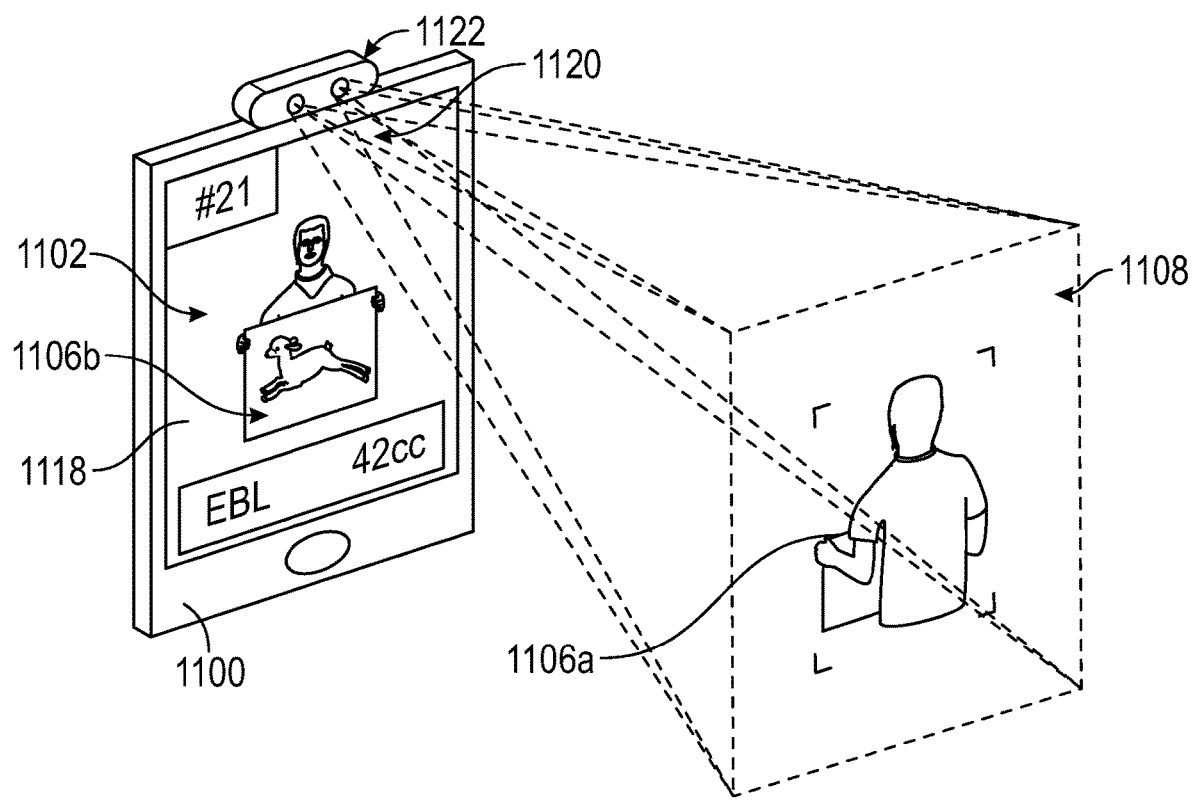
FIG. 12 is a schematic diagram depicting a method of analyzing a surgical textile, according to some example embodiments.

In certain example embodiments of the methods discussed herein, the one or more images (e.g., depicting one or more surgical items, one or more counting bags, or any suitable combination thereof) may analyzed to estimate a patient status (e.g., total blood loss, blood component loss, or both). For example, as depicted in FIG. 12, a computing device 1100 may acquire one or more images 1102 of a surgical textile using an imaging system 1122 with one or more cameras 1120. The one or more images 1102 may capture and depict a field of view 1108 that includes a surgical textile 1106*a*, such as a piece of surgical gauze, a surgical sponge, or a surgical towel. The surgical textile 1106*a* may be held by a user. As depicted in FIG. 12, the captured image, including an image 1106*b* of the surgical textile 1106*a*, may be displayed on a display 1118, such as on the computing device 1100. The one or more images 1102 may include a color image, which may be analyzed to estimate blood content, blood component content, or both, in the imaged surgical textile. For example, as described in U.S. Pat. No. 8,897,523 which was incorporated above, a color-related feature (e.g., intensity) in the color image may be transformed into an estimation of an amount of blood or a blood component (e.g., a mass of hemoglobin, a volume of whole blood, or both) in the surgical textile 1106*a*, either locally or by a remote computer system for such processing.

Moreover, the one or more images 1102 may include a depth image (e.g., containing depth information based on infrared data, stereoscopic images, or both). Depth information from such a depth image may more easily distinguish an object located in the foreground from other objects in the background. The depth image may be analyzed (e.g., as described in U.S. Patent Publication 2017/0186160 which was incorporated above) to confirm the presence of the surgical textile 1106*a* in the image, after which the computing device 1100 can then index a local surgical textile counter. The local surgical textile counter may be used to verify a count of surgical items determined by any one or more of the methods described above (e.g., using image analysis of a counting bag) or as an independent method of counting surgical items.

Example Systems for Tracking Surgical Items

Also described herein are example systems for tracking surgical items. Such systems for tracking surgical items may include one or more components configured to determine the first count of surgical items. For example, such a system may include one or more imaging systems, one or more weighing systems (e.g., scales), or any suitable combination thereof, used to determine the first count of surgical items. Such systems may include one or more components configured to determine the second count of surgical items. For example, such a system may include one or more counting bags, each with one or more pockets, configured to contain one or more surgical items. Such systems may include additional equipment used to contain and process one or more surgical items. For example, such a system may include one or more collection containers to hold used surgical items, one or more stands to hold one or more counting bags, and one or more mounts to hold one or more mobile computing devices used for imaging, image processing, or both. Such a system may include one or more imaging systems configured to generate one or more images of one or more counting bags or other containers for surgical items. The imaging system used to obtain the first count may be the same imaging system used to obtain the second count. Such systems may include one or more processing components for use in determining the first count, the second count, or both, and to compare the first count to the second count. For example, such one or more processing components may be configured to analyze one or more images to identify surgical items appearing in an image, count the surgical items in the image, or both. Such one or more processing components may utilize one or more computational techniques, such as computer vision, machine learning, deep vision, or any suitable combination thereof, to analyze images to aid in the tracking of surgical items. Such components (e.g., processing components, imaging components, or both) may be implemented via one or more mobile computing devices, each of which may include one or more cameras or other image sensors, one or more processors, one or more displays, or any suitable combination thereof.

According to some example embodiments of the systems discussed herein, one or more of such computing devices may include, for example, a mobile device, such as a mobile phone, a smartphone, a tablet computer, a laptop computer, or any suitable combination thereof, each of which may include a camera, a processor, a display, or any suitable combination thereof. However, in certain example embodiments, some or all of the system components discussed herein may be separated as discrete interconnected devices or other components. For example, the camera, the display, or both, may be located substantially near a counting bag (e.g., in the operating room), while the processor may be at a remote location (e.g., in the operating room separate from the camera, the display, or both, or outside the operating room), communicating with the camera and the display through a wired or wireless communication network. One or more of such computing devices may be used to display information to one or more users. For example, a computing device may include one or more display screens that may display information related to one or more counts of surgical items, one or more patient parameters, one or more medical procedures, the hospital, the operating room, patient blood loss, user compliance, any suitable combination thereof, or any of the information described above. One or more of such computing devices may be configured to provide audio information to one or more users.

One or more processors may be configured to perform some or all of any one or more of the methods described herein. For example, one or more of such processors may be configured to receive one or more images, perform one or more computational algorithms (e.g., computer vision, machine learning, deep learning, or any suitable combination thereof) to analyze such images, receive and analyze data (e.g. from user input or from computer memory), trigger one or more responses, or any suitable combination thereof. One or more of such processors may be configured to receive and analyze one or more images that depict one or more surgical items, one or more images that depict one or more counting bags, weight information, time stamp data (e.g., paired with weight information), user input, or any suitable combination thereof, to determine the first and second counts of surgical items. One or more of such processors may be configured, for example, to execute one or more machine learning algorithms to analyze one or more images to determine the number of surgical items shown in the one or more images. One or more of such processors may be configured to update an intermediate count of surgical items based on the number of surgical items appearing in the one or more images. One or more of such processors may be configured to determine the final count of surgical items, and such determining of the final count may include receiving manual input from a user. One or more of such processors may be configured to compare the first count of surgical items to the second count of surgical items (e.g. an intermediate count or the final count). One or more of such processors may be configured to generate a notification (e.g., an alert) based on the comparison of the first count to the second count. If the first count and second count do not match, one or more of such processors may be configured to generate or display an alert or other notification. Additionally or alternatively, one or more of such processors may perform one or more additional tasks related to determining counts of other items (e.g., used vs, unused items), tracking compliance information, receiving user input, triggering one or more responses to situations that occur during the medical procedure, sending information and alerts to appropriate personnel, or any suitable combination thereof.

Generally, any one or more of the processors discussed herein may be configured to execute instructions that are stored in memory such that, when it executes the instructions, the one or more processors perform one or more operations of one or more of the methods described herein. The instructions may be executed by computer-executable components integrated with the application, applet, host, server, network, website, communication service, communication interface, hardware elements, firmware elements, software elements, or any suitable combination thereof, of a user computer, a mobile device, a wristband, a smartphone, or any suitable combination thereof. The instructions may be stored on memory or other computer-readable medium such as RAMs, ROMs, flash memory, EEPROMs, optical devices (e.g., CD or DVD), hard drives, floppy drives, or any suitable device.

One or more processors configured to perform some or all of any one or more of the methods discussed herein may be integrated into a handheld or mobile computing device or may be implemented as external processors. In some example embodiments, one or more of such processors may be incorporated into a computer device or system, such as a cloud-based computer system, a mainframe computer system, a grid-computer system, or other suitable computer system. One or more of the systems discussed herein may include communication means to communicate data to one or more external processors. Additionally or alternatively, one or more of such processors may be incorporated into a remote server that receives images of surgical items, reconstructs or analyzes the images as described above, and transmits information related to the tracking of surgical items.

As described above, one or more example embodiments of the systems discussed herein may include one or more imaging systems. For example, such a system may include a camera that functions to generate one or more images of surgical items (e.g., surgical items contained in one or more counting bags), such as a set of one or more still images or part of a video feed. The one or more images may include a color image, a depth image (e.g., infrared, stereoscopic, ultrasound, etc.), a hyperspectral image, another suitable kind of image, or any suitable combination thereof. The camera may include at least one optical image sensor (e.g., CCD, CMOS, etc.) that captures a color optical digital image with red, green, and blue (RGB) color components for the pixels, or one or more other suitable optical components. For example, the camera may include a single image sensor paired with suitable corresponding optics, filters (e.g., color filter arrays such as a Bayer pattern filter), or both. As another example, the camera may include multiple image sensors paired with suitable corresponding optics, such as at least one prism or diffractive surface to divide white light into separate color channels (e.g., RGB), each of which is detected by a respective image sensor. One or more imaging systems, one or more computational processing tools, or any suitable combination thereof, may be configured on the same device, or an imaging system may be a separate component that communicates image data to one or more other components. One or more of such imaging systems may be a part of a mobile device (e.g. a camera on a smartphone), which may or may not be configured to implement one or more of the processing components described above. Such an imaging system may be configured to transmit images to one or more processors for analysis, a database that stores the images (e.g., cloud storage), or both.

One or more example embodiments of the systems discussed herein may include a display that functions to display or otherwise communicate information to a user (e.g., a doctor, a nurse, other medical personnel, or any suitable combination thereof), including patient information, one or more images of surgical items, one or more quantified metrics related to an accounting of surgical items, one or more notifications of a comparison between a first and second count (e.g., final count) of surgical items, a predetermined protocol for users to follow in the event that the first count and the second count of surgical items do not match, one or more measures of likelihood of duplicate imaging of surgical items (e.g., surgical textiles), a value of an index counter for a surgical item, one or more warnings or prompts to the user indicating potential duplicate imaging of surgical items, one or more summary reports, or any suitable combination thereof. The display may include a screen on a handheld or mobile device, a computer monitor, a television screen, a projector screen, or other suitable display. The display may be integrated in the same device as one or more components of the system. Additionally or alternatively, the display may include a standalone separate monitor, screen, or other suitable display.

According to some example embodiments, the display may be configured to display a user interface (e.g., a graphical user interface) that enables the user to interact with displayed information. For example, the user interface may enable the user to manipulate one or more of the images (e.g., zoom, crop, rotate, or any suitable combination thereof) or manually define the image region depicting at least a portion of a surgical item. As another example, the user interface may enable the user to select one or more display options (e.g., font, color, language, or any suitable combination thereof), select content (e.g., patient information, quantified metrics or other fluid-related information, alerts, etc.), or both. As yet another example, the user interface may enable the user to select one or more images for deletion due to depiction of a duplicate surgical item, or rotate, flip, or otherwise manipulate one or more images on the display. The display may be user-interactive and include a resistive or capacitive touch screen that is responsive to skin, a stylus, or other user contact. The display may be user-interactive via a cursor controlled by a mouse, keyboard, or other input device. For example, the display may allow the user to manually input information indicative of the first count, the second count, patient information, or any suitable combination thereof.

One or more example embodiments of the systems discussed herein may include a speaker or other suitable audio system that communicates information related to an accounting of surgical items (e.g. the first count or the second count), a value of an index counter for a surgical item, one or more notifications of a comparison between a first and second count (e.g., final count) of surgical items, a predetermined protocol for users to follow in the event that the first count and the second count of surgical items do not match, one or more measures of likelihood of duplicate imaging of surgical items, one or more warnings or prompts to the user indicating potential duplicate imaging of surgical items, one or more summary reports, or any suitable combination thereof. The display, the audio system, or both, may provide one or more notifications or alerts upon the first count not matching the second count (e.g. a final count), which may be useful to prompt certain actions in response, such as prompting a user to begin a specified protocol. As another example, the display, the audio system, or both, may provide one or more alerts or prompts to the user indicating a likelihood that two or more images depict the same surgical item, which may be useful to prompt the user to confirm whether duplicate imaging has occurred, re-assess locations of counted or uncounted surgical items, or any suitable combination thereof.

One or more example embodiments of the systems discussed herein may include items and equipment for use in surgical item counting methods. For example, such a system may include one or more collection containers, one or more counting bags for use in tracking and counting surgical items, one or more stands configured to hold counting bags, one or more mounts configured to hold one or more imaging systems (e.g., a mobile device), one or more weight detection components coupled to one or more components of the system, or any suitable combination thereof.

One or more example embodiments of the systems discussed herein may include one or more collection containers for use in collecting surgical items, such as surgical textiles. Collection containers may be used by medical personnel to place used items in, prior to counting (e.g., after a textile is used). Collection containers (e.g., "kick buckets") may be of any suitable size, shape, or material. A collection container may have a circular cross section. A collection container may be or include a small bucket-like container and may include a liner. A collection container may be made of metal, plastic, or any suitable material. The liner of a collection container may be of any suitable material. For example, the liner may be a transparent plastic liner. A transparent liner may provide the benefit of facilitating easy visualization of both soiled and clean surgical items. A collection container may be of any suitable size and may accommodate any suitable number of surgical items. Some example embodiments of such systems may include one or more collection containers, placed at various locations throughout the operating room. For example, one or more collection containers may be placed near the operating table to allow a doctor or a nurse to easily discard surgical items after use.

One or more example embodiments of the systems discussed herein may include one or more counting bags for use in containing and counting surgical items. For example, as described above, a counting bag may include a backing and one or more pockets configured to contain one or more surgical items. Counting bags may be of any suitable size, and such systems may include one or more counting bags of various sizes. For example, different counting bags may be sized to accommodate different types of surgical items (e.g., differently sized surgical textiles). Different types of surgical textiles come in different sizes, and counting bags may be appropriately sized to accommodate any suitable number and any suitable type of surgical textile. For example, a counting bag may be sized to accommodate between 1 and 30 surgical textiles. Similarly, a counting bag may have any suitable number of pockets to accommodate any suitable number of surgical textiles. Although textile counting protocols generally involve placing one surgical textile per pocket, a counting bag's pockets may be configured to accommodate any suitable number of surgical textiles. Further, a counting bag's pockets may be of sufficient size and shape to accommodate various types of surgical textiles. For example, a counting bag's pockets may be configured to accommodate various sizes of surgical textiles, such as surgical textiles with sizes in the range of 4 inches by 4 inches, to 18 inches by 18 inches. A counting bag's pockets may also be configured to accommodate various types of surgical textiles, such as laparotomy textiles (e.g., surgical textiles for laparotomy).

One or more example embodiments of the systems discussed herein for tracking surgical items may include one or more stands, such as a pole with one or more hooks, mounts, or any suitable combination thereof. A stand may include one or more mounts for holding one or more imaging devices (e.g., mobile devices). Such systems may include one or more counting bags, each configured to contain surgical items, such as surgical textiles, and aid one or more users in implementing one or more counting protocols for the surgical items. As described above (e.g., in reference to FIG. 4), a counting bag may include a backing and one or more pockets. The backing may include one or more openings configured to interact with the one or more hooks of the pole to hang the counting bag from the one or more hooks.

Counting bag components (e.g., the backing and the pockets) may be made of any suitable material and may have any suitable coloring. For example, the backing of a counting bag may have an opaque blue color, an opaque white color, or other suitable color, and the pockets may be made of a transparent material. It may be beneficial for the backing of one or more counting bags to be opaque and colored such that the counting bags are easily identifiable, even when stacked (e.g., one on top of each other), so that the color contrasts with both soiled and clean surgical items placed therein (e.g., soiled and clean surgical textiles). Further, transparent pockets may be beneficial to allow for visualization of surgical items within the pockets, visualization of one or more markers on the surgical items (e.g., tags on surgical textiles), or both. A counting bag may be of any suitable shape and size, such as a shape and size beneficial for hanging the counting bag from a pole. Although the example embodiment shown in FIG. 4 uses rectangular counting bags with rectangular pockets, a counting bags and its pockets can be of any suitable shape and size, as described above.

One or more example embodiments of the systems discussed herein for tracking surgical items may include one or more weight detection components. Such weight detection components may be used to sense the presence of surgical items, weigh them, count them, or any suitable combination thereof. As described above, one or more weight detection components may include one or more scales used to determine the first count of surgical items. For example, one or more weight detection components may be configured to receive the first count of surgical items and communicate weight information to a processor to determine the first count. One or more weight detection components may also be coupled to or incorporated with one or more collection containers (e.g., counting bags or "kick buckets") to determine the second count of surgical items. One or more collection containers may be coupled to, or may include, a scale or other suitable weight detection component to sense the weight decrement when a user removes a surgical item from the one or more collection containers. One or more counting bags may be coupled to one or more weight detection components in the example form of one or more strain gauges or scales coupled to a pole to sense a weight change when a surgical item is added to a counting bag, to determine the second count of surgical items.

The foregoing description, for purposes of explanation, used specific nomenclature to provide a thorough understanding of the present subject matter. However, it will be apparent to one skilled in the art that specific details are not required in order to practice the present subject matter. Thus, the foregoing descriptions of specific example embodiments are presented for purposes of illustration and description. They are not intended to be exhaustive or to limit the present subject matter to the precise forms disclosed. Many modifications and variations are possible in view of the above teachings. The example embodiments were chosen and described to explain the principles of the present subject matter and some of its practical applications, and they thereby enable others skilled in the art to utilize the present subject matter and various example embodiments with various modifications as are suited to the particular use contemplated. It is intended that the claims and their equivalents define the scope of the invention.

The following enumerated descriptions describe various examples of methods, machine-readable media, and systems (e.g., machines, devices, or other apparatus) discussed herein.

A first example provides a method of tracking surgical items, the method comprising:
at one or more processors:
receiving a first count of surgical items;
receiving one or more images, wherein each image is of a field of view comprising one or more surgical items;
determining a second count of surgical items based at least in part on the one or more received images; and
providing a notification based on a comparison between the first count of surgical items and the second count of surgical items.

A second example provides a method according to the first example, wherein the determining of the second count of surgical items comprises identifying one or more surgical items in the one or more received images.

A third example provides a method according to the second example, wherein at least one of the received images is a depth image.

A fourth example provides a method according to the third example, wherein the depth image is an infrared image.

A fifth example provides a method according to any of the second through fourth examples, wherein at least one of the received images is a color image.

A sixth example provides a method according to any of the second through fifth examples, wherein the surgical item is a surgical textile.

A seventh example provides a method according to any of the second through sixth examples, wherein the identifying of the one or more surgical items comprises identifying and characterizing a container comprising one or more compartments in the one or more images.

An eighth example provides a method according to the seventh example, wherein the container comprises a backing and a plurality of pockets arranged on the backing in a rectangular grid.

A ninth example provides a method according to the eighth example, wherein the plurality of pockets comprise a transparent material.

A tenth example provides a method according to the eighth example, wherein, the backing comprises an opaque material.

An eleventh example provides a method according to any of the seventh through tenth examples, wherein the characterizing of the container comprises determining one or more parameters of the container.

A twelfth example provides a method according the eleventh example, wherein the determining of the one or more parameters of the identified container comprises quantifying the one or more compartments of the container.

A thirteenth example provides a method according to the eleventh example or the twelfth example, wherein the determining of the one or more parameters of the identified container comprises determining a geometrical arrangement of the one or more compartments of the container.

A fourteenth example provides a method according to any of the eleventh through thirteenth examples, wherein the determining of the one or more parameters of the identified container comprises determining presence or absence of a surgical item in each of the one or more compartments of the container.

A fifteenth example provides a method according to any of the first through fourteenth examples, wherein the determining of the second count of surgical items is further based at least in part on detecting a change in weight of a container configured to hold one or more surgical items.

A sixteenth example provides a method according to any of the first through fifteenth examples, wherein the receiving of the first count of surgical items comprises identifying one or more surgical items in an image.

A seventeenth example provides a method according to any of the first through sixteenth examples, wherein the receiving of the first count of surgical items is based at least in part on detecting a weight of one or more surgical items.

An eighteenth example provides a method according to any of the first through seventeenth examples, wherein the first count of surgical items is provided through a user input.

A nineteenth example provides a method according to any of the first through eighteenth examples, wherein the determining of the second count of surgical items comprises updating a current index value of surgical items.

A twentieth example provides a method according to the nineteenth example, further comprising displaying the current index value of surgical items on a display.

A twenty-first example provides a method according to any of the first through twentieth examples, further comprising prompting a user to verify the accuracy of at least one of the first count and the second count.

A twenty-second example provides a method according to any of the first through twenty-first examples, further comprising displaying at least one of the first count of surgical items, the second count of surgical items, or the notification on a display.

A twenty-third example provides a method according to any of the first through twenty-second examples, further comprising providing a summary report of tracked surgical items.

A twenty-fourth example provides a method according to any of the first through twenty-third examples, wherein the providing of the notification based on the comparison between the first count and the second count comprises generating an alert in response to the first count not matching the second count.

A twenty-fifth example provides a method according to the twenty-fourth example, wherein the alert is in accordance with a predetermined protocol.

A twenty-sixth example provides a method according to any of the first through twenty-fifth examples, wherein at least a portion of the first count is received before a medical procedure.

A twenty-seventh example provides a method according to any of the first through twenty-sixth examples, wherein the second count is determined during or after a medical procedure.

A twenty-eighth example provides a method according to any of the first through twenty-seventh examples, wherein the determining of the second count comprises using one or more machine learning models to analyze the one or more received images.

A twenty-ninth example provides a method according to the twenty-eighth example, wherein one or more of the machine learning models incorporates a deep learning technique.

A thirtieth example provides a system for tracking surgical items, the system comprising:
one or more processors configured to perform operations comprising: receiving a first count of surgical items; receiving one or more images, wherein each image is of a field of view comprising one or more surgical items; determining a second count of surgical items based at least in part on the one or more received images; and providing a notification based on a comparison between the first count of surgical items and the second count of surgical items.

A thirty-first example provides a system according to the thirtieth example, wherein the determining of the second count of surgical items comprises identifying one or more surgical items in the one or more received images.

A thirty-second example provides a system according to the thirty-first example, wherein at least one of the received images is a depth image.

A thirty-third example provides a system according to the thirty-second example, wherein the depth image is an infrared image.

A thirty-fourth example provides a system according to any of the thirty-first through thirty-third examples, wherein at least one of the received images is a color image.

A thirty-fifth example provides a system according to any of the thirty-first through thirty-fourth examples, wherein the identifying of the one or more surgical items comprises identifying and characterizing a container comprising one or more compartments in the one or more images.

A thirty-sixth example provides a system according to the thirty-fifth example, wherein the characterizing of the container comprises determining one or more parameters of the container.

A thirty-seventh example provides a system according the thirty-sixth example, wherein the determining of the one or more parameters of the identified container comprises quantifying the one or more compartments of the container.

A thirty-eighth example provides a system according to the thirty-sixth example or the thirty-seventh example, wherein the determining of the one or more parameters of the identified container comprises determining a geometrical arrangement of the one or more compartments of the container.

A thirty-ninth example provides a system according to any of the thirty-sixth through thirty-eighth examples, wherein the determining of the one or more parameters of the identified container comprises determining presence or absence of a surgical item in each of the one or more compartments of the container.

A fortieth example provides a system according to any of the thirty-fifth through thirty-ninth examples, wherein the container is a flexible container comprising a backing and a plurality of pockets arranged in a rectangular grid.

A forty-first example provides a system according to the fortieth example, wherein the plurality of pockets comprise a transparent material.

A forty-second example provides a system according to the fortieth example, wherein the backing comprises an opaque material.

A forty-third example provides a system according to any of the thirtieth through forty-second examples, further comprising an optical sensor configured to generate the one or more images received by the processor.

A forty-fourth example provides a system according to any of the thirtieth through forty-third examples, further comprising a display screen.

A forty-fifth example provides a system according to the forty-fourth example, wherein the display screen is configured to display a summary report of tracked surgical items.

A forty-sixth example provides a system according to the forty-fourth example or the forty-fifth example, wherein the display screen is configured to display the notification based on the comparison between the first count and the second count.

A forty-seventh example provides a system according to the forty-sixth example, wherein the notification comprises an alert in accordance with a predetermined protocol if the first count does not match the second count.

A forty-eight example provides a system according to any of the thirtieth through forty-seventh examples, wherein the surgical item is a surgical textile.

A forty-ninth example provides a system according to any of the thirtieth through forty-eighth examples, wherein at least one of the one or more processors is in a mobile computing device removably mounted to a stand.

A fiftieth example provides a method for tracking surgical items, the method comprising:
at one or more processors:
receiving an image of a field of view, wherein the field of view comprises one or more surgical items;
determining the presence of the one or more surgical items in the image; and
providing an indication of the determined presence of the one or more surgical items in the image.

A fifty-first example provides a method according to the fiftieth example, further comprising quantifying the one or more surgical items in the image based on at least one trained machine learning model.

A fifty-second example provides a method according to the fifty-first example, wherein the machine learning model incorporates a deep learning technique.

A fifty-third example provides a method according to any of the fiftieth through fifty-second examples, wherein the determining of the presence of the one or more surgical items comprises detecting the presence of a container in the image, wherein the container comprises a plurality of compartments, each compartment configured to receive at least one respective surgical item.

A fifty-fourth example provides a method according to the fifty-third example, further comprising classifying each compartment based on the presence or absence of a surgical item.

A fifty-fifth example provides a method according to any of the fiftieth through fifty-fourth examples, wherein the providing of the indication of the determined presence comprises providing an indication of a determined presence of at least one surgical item in the image.

A fifty-sixth example provides a method according to any of the fiftieth through fifty-fifth examples, wherein the one or more surgical items comprises a surgical textile.

A fifty-seventh example provides a method according to any of the fiftieth through fifty-sixth examples, wherein the one or more surgical items comprises a surgical instrument.

A fifty-eighth example provides a carrier medium carrying machine-readable instructions for controlling a machine to carry out the operations (e.g., method operations) performed in any one of the previously described examples.

A fifty-ninth example provides a machine-readable medium (e.g., a non-transitory machine-readable storage medium) comprising instructions that, when executed by one or more processors of a machine, cause the machine to perform the operations (e.g., method operations) specified by any one of the previously described examples.

What is claimed is:

1. A method comprising:
determining, by one or more processors, a first count of surgical items, the first count quantifying a set of surgical items;
accessing, by the one or more processors, an image that depicts at least a subset of the set of surgical items;
determining, by the one or more processors, a second count of surgical items by characterizing a container that includes a set of compartments depicted in the image; and
providing, by the one or more processors, a notification based on a comparison of the first count of surgical items and the second count of surgical items;
wherein the one or more processors are configured to characterize the container by:
converting, with a counting bag geometry model, the image into a plurality of pocket images, each pocket image corresponding to a portion of the image which includes a compartment of the set of compartments; and
determining the second count of the surgical items based on the pocket images.

2. The method of claim 1, wherein:
the determining of the first count of surgical items includes identifying the set of surgical items from a further image.

3. The method of claim 1, wherein:
the providing of the notification based on the comparison of the first count and the second count includes providing an alert in response to the first count not matching the second count.

4. The method of claim 1, wherein characterizing the container includes classifying, with a pocket classifier model, each pocket image as corresponding to a full compartment or an empty compartment.

5. The method of claim 4, wherein determining the second count of the surgical items is based on an output from the pocket classifier model and includes determining the second count of the surgical items based on the classification of the pocket images.

6. The method of claim 1, wherein each pocket image includes a cropped image segment, each cropped image segment including the portion of the image that contains the corresponding compartment.

7. The method of claim 1, wherein each pocket image includes:
the image; and
a location of the corresponding compartment in the image.

8. The method of claim 1, further comprising displaying, on a display:
the image; and
a plurality of bounding boxes overlaid on the image, each of the bounding boxes surrounding one of the compartments.

9. A non-transitory machine-readable medium comprising instructions that, when executed by one or more processors of a machine, cause the machine to perform operations comprising:
determining a first count of surgical items, the first count quantifying a set of surgical items;
accessing an image that depicts at least a subset of the set of surgical items;
determining a second count of surgical items by characterizing a container that includes a set of compartments depicted in the image; and
providing a notification based on a comparison of the first count of surgical items and the second count of surgical items;
wherein characterizing the container includes:
converting, with a counting bag geometry model, the image into a plurality of pocket images, each pocket image corresponding to a portion of the image which includes a compartment of the set of compartments; and
determining the second count of the surgical items based on the pocket images.

10. The method of claim 9, wherein characterizing the container includes classifying, with a pocket classifier model, each pocket image as corresponding to a full compartment or an empty compartment.

11. The method of claim 10, wherein determining the second count of the surgical items is based on an output from the pocket classifier model and includes determining the second count of the surgical items based on the classification of the pocket images.

12. The non-transitory machine-readable medium of claim 9, wherein each pocket image includes a cropped image segment, each cropped image segment including the portion of the image that contains the corresponding compartment.

13. The non-transitory machine-readable medium of claim 9, wherein each pocket image includes:
 the image; and
 a location of the corresponding compartment in the image.

14. The non-transitory machine-readable medium of claim 9, further comprising instructions that, when executed by one or more processors of a machine, cause the machine to perform operations comprising displaying, on a display:
 the image; and
 a plurality of bounding boxes overlaid on the image, each of the bounding boxes surrounding one of the compartments.

15. A system comprising:
 one or more processors; and
 a memory storing instructions that, when executed by at least one processor among the one or more processors, cause the system to perform operations comprising:
 determining a first count of surgical items, the first count quantifying a set of surgical items;
 accessing an image that depicts at least a subset of the set of surgical items;
 determining a second count of surgical items by characterizing a container that includes a set of compartments depicted in the image; and
 providing a notification based on a comparison of the first count of surgical items and the second count of surgical items;
 wherein characterizing the container includes:
 converting, with a counting bag geometry model, the image into a plurality of pocket images, each pocket image corresponding to a portion of the image which includes a compartment of the set of compartments; and
 determining the second count of the surgical items based on the pocket images.

16. The method of claim 15, wherein characterizing the container includes classifying, with a pocket classifier model, each pocket image as corresponding to a full compartment or an empty compartment.

17. The method of claim 16, wherein determining the second count of the surgical items is based on an output from the pocket classifier model and includes determining the second count of the surgical items based on the classification of the pocket images.

18. The system of claim 15, wherein each pocket image includes a cropped image segment, each cropped image segment including the portion of the image that contains the corresponding compartment.

19. The system of claim 15, wherein each pocket image includes:
 the image; and
 a location of the corresponding compartment in the image.

20. The system of claim 15, wherein the instructions, when executed by at least one processor among the one or more processors, further cause the system to perform operations comprising displaying, on a display:
 the image; and
 a plurality of bounding boxes overlaid on the image, each of the bounding boxes surrounding one of the compartments.

* * * * *